(12) United States Patent
Newell et al.

(10) Patent No.: US 8,329,753 B2
(45) Date of Patent: Dec. 11, 2012

(54) COMBINATION OF COMPOUNDS, OR A BIFUNCTIONAL COMPOUND, THAT PROVIDES FATTY ACID METABOLISM AND GLYCOLYSIS INHIBITION

(75) Inventors: Martha Karen Newell, Colorado Springs, CO (US); Evan Newell, Menlo Park, CA (US)

(73) Assignee: The Regents of the University of Colorado, Denver, CO (US)

( * ) Notice: Subject to any disclaimer, the term of this patent is extended or adjusted under 35 U.S.C. 154(b) by 755 days.

(21) Appl. No.: 11/919,734

(22) PCT Filed: Apr. 20, 2006

(86) PCT No.: PCT/US2006/015124
§ 371 (c)(1),
(2), (4) Date: Mar. 5, 2009

(87) PCT Pub. No.: WO2006/118821
PCT Pub. Date: Nov. 9, 2006

(65) Prior Publication Data
US 2011/0015262 A1  Jan. 20, 2011

Related U.S. Application Data

(60) Provisional application No. 60/676,861, filed on May 2, 2005.

(51) Int. Cl.
*A61K 31/18* (2006.01)
(52) U.S. Cl. .................................................... 514/603
(58) Field of Classification Search .................... 514/603
See application file for complete search history.

(56) References Cited

U.S. PATENT DOCUMENTS

| | | | |
|---|---|---|---|
| 2,956,076 A * | 10/1960 | Carbon et al. | 560/124 |
| 5,587,397 A | 12/1996 | Fox | |
| 6,331,559 B1 | 12/2001 | Bingham et al. | |
| 6,569,853 B1 | 5/2003 | Borisy et al. | |
| 6,670,330 B1 | 12/2003 | Lampidis et al. | |
| 6,846,816 B2 | 1/2005 | Borisy et al. | |
| 6,951,887 B2 | 10/2005 | Bingham et al. | |
| 2002/0107234 A1 | 8/2002 | Bingham et al. | |
| 2003/0212138 A1 | 11/2003 | Obukowicz | |
| 2004/0005291 A1 | 1/2004 | Rogers et al. | |
| 2004/0116407 A1 | 6/2004 | Borisy et al. | |
| 2005/0020682 A1 | 1/2005 | Newell et al. | |
| 2005/0042224 A1 | 2/2005 | Newell et al. | |
| 2005/0074882 A1 | 4/2005 | Newell et al. | |
| 2005/0158333 A1 | 7/2005 | Newell | |
| 2005/0202559 A1 | 9/2005 | Pownall et al. | |
| 2006/0140953 A1 | 6/2006 | Newell et al. | |
| 2006/0247199 A1 | 11/2006 | Newell et al. | |

FOREIGN PATENT DOCUMENTS

| | | |
|---|---|---|
| EP | 0 239 400 B1 | 9/1987 |
| WO | WO 01/34145 A1 | 5/2001 |
| WO | WO 2004/111199 A2 | 12/2004 |
| WO | WO 2004111199 A2 * | 12/2004 |

OTHER PUBLICATIONS

Alberts et al., Molecular Biology of the Cell. 4th Ed. Garland Science, 2002, NY. 856-7. Fig 15-32.
Baselga et al., Antitumor effects of doxorubicin in combination with anti-epidermal growth factor receptor monoclonal antibodies. J Natl Cancer Inst. Aug 18, 1993;85(16):1327-33. Abstract Only.
Black et al., Glycolytic enzyme inhibitor therapy in human malignant neoplasia. Cancer Res. May 1949;9(5):314-9.
Bull, Mode of action of liver tumor induction by trichloroethylene and its metabolites, trichloroacetate and dichloroacetate. Environ Health Perspect. May 2000;108 Suppl 2:241-59.
Cabrero et al., Uncoupling protein-3 mRNA up-regulation in C2C12 myotubes after etomoxir treatment. Biochim Biophys Acta. Jun. 29, 2001;1532(3):195-202.
Calkins et al., UNL Beef Cattle Reports. Univ. of Nebraska Cooperative Extension-MP71. Beef. Feb. 1999.
Clement et al., Superoxide anion is a natural inhibitor of FAS-mediated cell death. EMBO J. Jan. 15, 1996;15;15(2):216-25.
Costantini et al., Mitochondrion as a novel target of anticancer chemotherapy. J Natl Cancer Inst. Jul. 5, 2000;92(13):1042-53.
Dulloo et al., Uncoupling protein 3 and fatty acid metabolism. Biochem Soc Trans. Nov. 2001;29(Pt 6):785-91.
Fantin et al., A novel mitochondriotoxic small molecule that selectively inhibits tumor cell growth. Cancer Cell. Jul. 2002;2(1):29-42.
Harper et al., Characterization of a novel metabolic strategy used by drug-resistant tumor cells. FASEB J. Oct. 2002;16(12):1550-7. Harrington-Brock et al., Mutagenicity of three disinfection by-products: di- and trichloroacetic acid and chloral hydrate in L5178Y/TK x/-31 (-)3.7.2C mouse lymphoma cells. Mutat Res. Mar. 30, 1998;413(3):265-76. Abstract Only.
Healy et al., Glucose, but not glutamine, protects against spontaneous and anti-Fas antibody-induced apoptosis in human neutrophils. Clin Sci (Lond). Aug. 2002;103(2):179-89.
Huppertz et al., Uncoupling protein 3 (UCP3) stimulates glucose uptake in muscle cells through a phosphoinositide 3-kinase-dependent mechanism. J Biol Chem. Apr. 20, 2001;276(16):12520-9. Epub Jan. 12, 2001.
Johnson et al., Relationships between drug activity in NCI preclinical in vitro and in vivo models and early clinical trials. Br J Cancer. May 18, 2001;84(10):1424-31.
Kaplan et al., Effects of 2-deoxyglucose on drug-sensitive and drug-resistant human breast cancer cells: toxicity and magnetic resonance spectroscopy studies of metabolism. Cancer Res. Feb. 1, 1990;50(3):544-51.

(Continued)

*Primary Examiner* — Kevin E Weddington
(74) *Attorney, Agent, or Firm* — Wolf, Greenfield & Sacks, P.C.

(57) ABSTRACT

Methods and compositions for treating inflammatory and proliferative diseases, enabling treatment of MDR tumor cells by using combination of compounds, or a bifunctional compound, that inhibits both fatty acid metabolism and glycolysis. In particular, the invention combines or links a glycolysis inhibitor that is, or that is derived from, hypoglycin A (also referred to as hypoglycine A) and a fatty acid metabolism inhibitor. Preferably, the invention provides bifunctional compounds that link a moiety having the functionality of an oxirane carboxylic acid compound to a moiety having the functionality a hypoglycin A derivative. In specific embodiments, the invention provides a bifunctional compound that links a moiety having the functionality of etomoxir to a moiety having the functionality of hypoglycin A.

6 Claims, 9 Drawing Sheets

OTHER PUBLICATIONS

Koop et al., Continuous bioluminescent monitoring of cytoplasmic ATP in single isolated rat hepatocytes during metabolic poisoning. Biochem J. Oct. 1, 1993;295 ( Pt 1):165-70.

Kuhajda et al., Synthesis and antitumor activity of an inhibitor of fatty acid synthase. Proc Natl Acad Sci U S A. Mar. 28, 2000;97(7):3450-4.

Li et al., Induction of uncoupling protein 2 mRNA in beta-cells is stimulated by oxidation of fatty acids but not by nutrient oversupply. Endocrinology. Apr. 2002;143(4):1371-7.

Mills et al., Regulation of cellular oncosis by uncoupling protein 2. J Biol Chem. Jul. 26, 2002;277(30):27385-92. Epub May 14, 2002.

Molero et al., Recovery of polyols from flexible polyurethane foam by "split-phase" glycolysis: Glycol influence. Polymer Degradation and Stability. Feb. 2006;91(2):221.

Newell et al., The effects of chemotherapeutics on cellular metabolism and consequent immune recognition. J Immune Based Ther Vaccines. Feb. 2, 2004;2(1):3.

Ohta et al., Augmentation of anti-Fas antibody-mediated apoptosis on human glioma cells by liposomes associated with the antibody. J Neurooncol. Oct. 1997;35(1):7-11. Abstract Only.

Patane et al., Role of ATP production and uncoupling protein-2 in the insulin secretory defect induced by chronic exposure to high glucose or free fatty acids and effects of peroxisome proliferator-activated receptor-gamma inhibition. Diabetes. Sep. 2002;51(9):2749-56.

Samec et al., Skeletal muscle UCP3 and UCP2 gene expression in response to inhibition of free fatty acid flux through mitochondrial beta-oxidation. Pflugers Arch. Sep. 1999;438(4):452-7.

Sausville et al., Contributions of human tumor xenografts to anticancer drug development. Cancer Res. Apr. 1, 2006;66(7):3351-4, discussion 3354.

Saydjari et al., 2-Deoxy-D-glucose inhibits the antitumor effects of alpha- difluoromethylornithine on the growth of colon cancer in vivo. Invest New Drugs. Jul. 1989;7(2-3):131-8.

Strieleman et al., Fatty acid activation of the reconstituted brown adipose tissue mitochondria uncoupling protein. J Biol Chem. Nov. 5, 1985;260(25):13402-5.

Tao et al., Effect of dichloroacetic acid and trichloroacetic acid on DNA methylation in liver and tumors of female B6C3F1 mice. Toxicol Sci. Jun. 1998;43(2):139-44. Abstract Only.

Thupari et al., Fatty acid synthase inhibition in human breast cancer cells leads to malonyl-CoA-induced inhibition of fatty acid oxidation and cytotoxicity. Biochem Biophys Res Commun. Jul. 13, 2001;285(2):217-23. Erratum in: Biochem Biophys Res Commun Jul. 12, 2002;295(2):570.

Timmer et al., Fas receptor-mediated apoptosis: a clinical application? J Pathol. Feb. 2002;196(2):125-34. Abstract Only.

Tschmelitsch et al., Enhanced antitumor activity of combination radioimmunotherapy (1311-labeled monoclonal antibody A33) with chemotherapy (fluorouracil). Cancer Res. Jun. 1, 1997;57(11):2181-6.

Zhelev et al., Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.

* cited by examiner (I)

(II)

(III)

(XIII)

(XIV)

(XV)

(XVI)

(XVII)

(XVIII)

(XIX)

(XX)

(XXI)

(XXII)

(XXIII)

(XXIV)

(XXV)

(XXVI)

(XXVII)

COMBINATION OF COMPOUNDS, OR A BIFUNCTIONAL COMPOUND, THAT PROVIDES FATTY ACID METABOLISM AND GLYCOLYSIS INHIBITION

This application is a National Stage Application of PCT/US2006/015124, filed Apr. 20, 2006, which claims priority under 35 U.S.C. §119(e) to U.S. Provisional Application Ser. No. 60/676,861, entitled "SYSTEMS AND METHODS FOR TREATING HUMAN INFLAMMATORY AND PROLIFERATIVE DISEASES, WITH A COMBINATION OF COMPOUNDS, OR A BIFUNCTIONAL COMPOUND, THAT PROVIDES FATTY ACID METABOLISM AND GLYCOLYSIS INHIBITION" filed on May 2, 2005, which is herein incorporated by reference in its entirety.

FIELD OF INVENTION

This invention generally relates to systems and methods for treating human inflammatory and proliferative disease.

BACKGROUND

Normal tissue develops, and is maintained by, processes of cell division and cell death. Diseases associated with increased cell division include cancer and atherosclerosis. It is commonly observed in treating cancers, that initial treatments, such as with chemotherapy and/or radiation therapy, are effective to destroy significant numbers of tumor cells, only to leave behind a small number of tumor cells that are resistant to the treatment, which then multiply to form newly detected tumors that are increasingly resistant to treatment as new rounds of therapy are tried. The growing popularity of "cocktails" of chemotherapy drugs has given rise to multi-drug resistant ("MDR") tumor cells, which are ever more difficult to destroy. Drug sensitive tumor cells, under the selective pressure of treatment with drugs, develop into drug resistant versions of the same tumor cell type. Drug resistance, either acquired or inherent, is the leading cause of death in cancer.

Methods for dealing with MDR tumor cells have been proposed, but without practical, clear clinical success at entirely eliminating such cells and providing a cure for patients with MDR tumors. For example, in Lampdis and Priebe U.S. Pat. No. 6,670,330, entitled: "Cancer Chemotherapy with 2-Deoxy-D-Glucose," incorporated herein in its entirety by reference, a class of glycolytic inhibitors are described for use in combination with standard chemotherapy protocols in treating solid tumors by attacking anaerobic cells a the center of the tumor. In Pizer, Townsend and Kuhajda U.S. Patent Publication No. 20020187534, published Dec. 12, 2002, entitled: "Treating cancer by increasing intracellular malonyl CoA levels," incorporated herein in its entirety by reference, fatty acid metabolism is manipulated by inhibition of carnitine palmitoyltransferase-1, for example with etomoxir.

SUMMARY OF INVENTION

The invention generally relates to systems and methods for treating inflammatory and proliferative diseases, enabling treatment of MDR tumor cells by using combination of compounds, or a bifunctional compound, that inhibits both fatty acid metabolism and glycolysis. In particular, the invention combines or links a glycolysis inhibitor that is, or that is derived from, hypoglycin A (also referred to as hypoglycine A) and a fatty acid metabolism inhibitor. Preferably, the invention provides bifunctional compounds that link a moiety having the functionality of an oxirane carboxylic acid compound to a moiety having the functionality a hypoglycin A derivative. In specific embodiments, the invention provides a bifunctional compound that links a moiety having the functionality of etomoxir to a moiety having the functionality of hypoglycin A.

In one set of embodiments, the invention provides a unique combination of compounds or, preferably, unique bifunctional compounds, alone or in combination with a pharmaceutically acceptable carrier In another set of embodiments, the invention includes exposing cells to the combination of compounds, or bifunctional compound, alone or in conjunction with other treating agents for treating cancer or to stimulate the wound healing process for enhancing wound healing.

Other advantages and novel features of the invention will become apparent from the following detailed description of the various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

Figure 1:
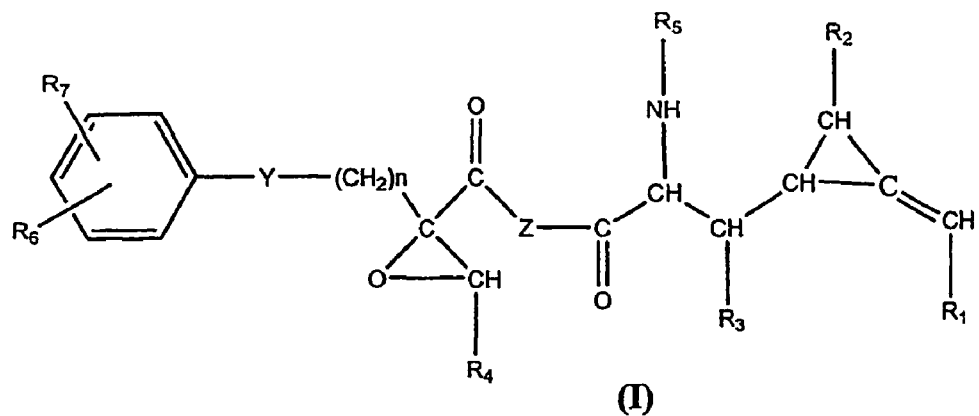
FIG. 1 shows generic chemical structures (I), (II), and (III) of a first set of three embodiments of bifunctional compounds of this invention.
Figure 1:
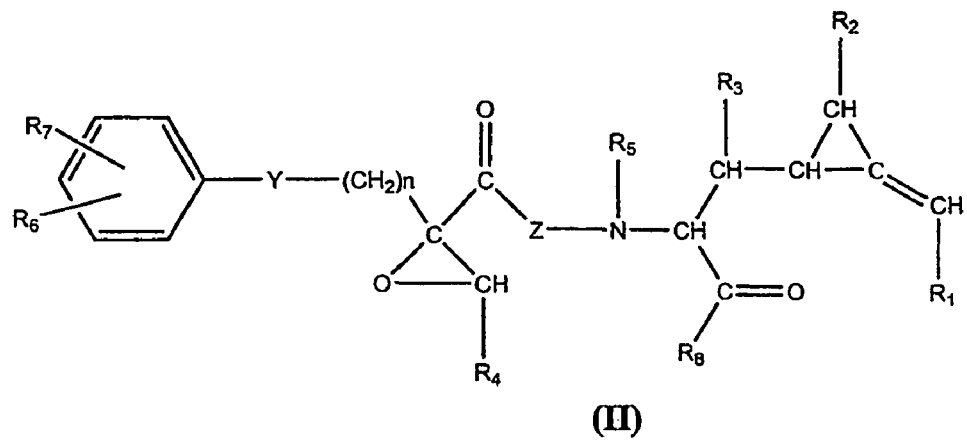
Figure 1:
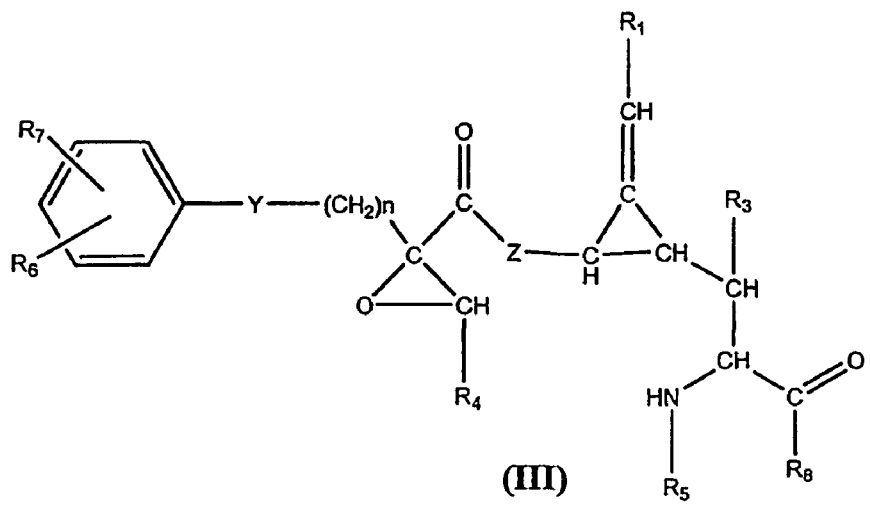

The present invention, proceeds by recognizing that cells have available to them a number of different metabolic pathways that are brought into play depending on the nature and degree of stress applied to the cells, that cell apoptosis is brought about to a significant extent because the target cells are recognized by the immune system, and that MDR cells are to a significant extent invisible to the immune system. The invention targets cellular metabolic pathways of defective cells, tissues or organs, and the immune system to treat human inflammatory and proliferative diseases, such as cancer, autoimmunity, heart disease, and chronic infectious disease. The methods herein are also useful in tissue regeneration, including neural regeneration, transplantation, and wound healing.

Every cell in the body uses carbohydrates, protein, and fat in different proportions for energy. The cell's choice of fuel, its metabolic strategy, will change depending on its state of activation or differentiation. For example, a cell that is rapidly dividing has different energy demands than one that is not dividing. The same is true for cells that are under stress or are infected. Drug resistant cells have a unique metabolic strategy characterized by the ability to burn fat under conditions of stress, including the stress of chemotherapy or radiation. When cells are rapidly dividing, they use glucose at very high rates, but under conditions of stress, cells, if capable, use fat in a greater proportion as a protective strategy. Respiration, oxygen use, and external stresses can generate a variety of toxic by-products (including free radicals) that can cause damage to cells. Tumor cells upregulate proteins that allow them to burn fat as a protective strategy against such by-products. The immune system can monitor the metabolic state of individual cells and destroy those in an inappropriate state. However, tumor cells can survive this surveillance by changing their metabolic strategy to one that protects the tumor cell by causing the cell to be virtually invisible to the immune system.

By inhibiting fatty acid metabolism, the cell is forced to resume glucose metabolism, thus exhibiting UCP and/or Fas on its cell surface to become visible to the immune system. Thus the invention generally relates to systems and methods for treating inflammatory and proliferative diseases using a combination of compounds or, preferably, a bifunctional compound having moieties that target predominant metabolic pathways: fatty acid metabolism and glycolysis. More specifically, the invention combines or links a glycolysis inhibitor that is, or that is derived from, hypoglycin A (also referred to as hypoglycine A) and a fatty acid metabolism inhibitor. Preferably, the invention provides bifunctional compounds that link a moiety having the functionality of an oxirane carboxylic acid compound to a moiety having the functionality a hypoglycin A derivative. In specific embodiments, the invention provides a bifunctional compound that links a moiety having the functionality of etomoxir to a moiety having the functionality of hypoglycin A.

Uncoupling proteins (UCPs) are often expressed in the plasma membrane of rapidly dividing cells. By manipulating UCP expression within cellular and intracellular membranes, inhibition of cellular, metabolic, and/or immunological responses may occur. In the present invention, the cells may be manipulated to increase the amount of cell surface Fas by exposure to a combination of compounds, or a bifunctional compound, under this invention having the functionality of a fatty acid metabolism inhibitor.

The following applications are incorporated herein by reference: U.S. Provisional Patent Application Ser. No. 60/566,746, filed Apr. 29, 2004, entitled "Systems and Methods for Treating Human Inflammatory and Proliferative Diseases, With a Combination of Fatty Acid Metabolism Inhibitors and Glycolytic Inhibitors and/or UCP and/or Fas antibodies", U.S. patent application Ser. No. 11/031,109, filed Jan. 7, 2005, entitled "Systems and Methods for Treating Human Inflammatory and Proliferative Diseases, With UCP and/or Fas Antibody or Other Inhibitor, Optionally With a Fatty Acid Metabolism Inhibitors and/or Glucose Metabolism Inhibitor", International Patent Application No. PCT/US2004/018612, filed Jun. 11, 2004, published as WO 2004/111199, entitled "Systems and Methods for Treating Human Inflammatory and Proliferative Diseases and Wounds, With Fatty Acid Metabolism Inhibitors and/or Glycolytic Inhibitors", and International Patent Application No. PCT/US2000/17245, filed Jun. 22, 2000, published as WO 2000/78941, entitled "Methods and Products for Manipulating Uncoupling Protein Expression."

The indefinite articles "a" and "an," as used herein in the specification and in the claims, unless clearly indicated to the contrary, should be understood to mean "at least one."

As used herein, "of" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

A "subject," as used herein, means a human or non-human mammal, including but not limited to, a dog, cat, horse, cow, pig, sheep, goat, chicken, primate, rat, and mouse.

The systems and methods of the invention have broad utility in regulating mammalian cell growth and death in vitro, in vivo, and ex vivo. The in vitro methods of the invention are useful for a variety of purposes. For instance, the systems and methods of the invention may be useful for identifying drugs, that have an effect, such as a preventative effect, on cellular division, cancers, or cell death, by contacting cells manipulated by the invention to undergo cellular division or death upon exposure to putative compounds.

In addition to in vitro methods, certain methods of the invention may be performed in vivo or ex vivo in a subject to manipulate one or more cell types within the subject. An "ex vivo" method, as used herein, is a method, that involves isolation of a cell from a subject, manipulation of the cell outside of the body, and reimplantation of the manipulated cell into the subject. The ex vivo procedure may be used on autologous or heterologous cells, and is typically used on autologous cells. In some embodiments, the ex vivo method is performed on cells that are isolated from bodily fluids, such as peripheral blood or bone marrow, however, the cells may be isolated from any source of cells. When returned to the subject, the manipulated cell can be programmed for cell death or division, depending on the treatment to which it was exposed. Ex vivo manipulation of cells has been described in several references in the art, including Engleman, *Cytotechnology*, 25:1, 1997, Van Schooten, et al., *Molecular Medicine Today*, June, 255, 1997, Steinman, *Experimental Hematology*, 24:849, 1996, and Gluckman, *Cytokines, Cellular and Molecular Therapy*, 3:187, 1997. The ex vivo activation of cells of the invention may be performed by routine ex vivo manipulation steps known in the art.

In vivo methods are also well known in the art. Thus, the invention is useful for therapeutic purposes as well as research purposes, such as testing in animal or in vitro models of certain medical, physiological or metabolic pathways or conditions.

In one form of the invention its most generic form, a fatty acid metabolism inhibitor is combined with hypoglycin A or a derivative of hypoglycin A. In another form of the invention, a moiety functioning as a fatty acid metabolism inhibitor is linked to a moiety functioning as hypoglcin A.

Preferably, the fatty acid inhibitor is, or the functionality of the fatty acid metabolism inhibitor is that of, an oxirane carboxylic acid compound able to inhibit (e.g., prevent, or at least decrease the activity by an order of magnitude or more)

a reaction within the fatty acid metabolism pathway, such as an enzyme-catalyzed reaction within the pathway. The inhibitor may inhibit the enzyme, e.g., by binding to the enzyme to interfere with operation of the enzyme (for example, by locking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.).

The fatty acid metabolism pathway includes several enzymatic reactions, for example, using enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc. In one set of embodiments, the fatty acid metabolism inhibitor is an inhibitor able to inhibit a beta-oxidation reaction in the fatty acid metabolism pathway. In another set of embodiments, the inhibitor is an inhibitor for a fatty acid transporter (e.g., a transporter that transports fatty acids into the cell, or from the cytoplasm into the mitochondria for metabolism), the inhibitor may react or otherwise inhibit key steps within the fatty acid metabolism pathway, or the inhibitor may be an inhibitor of fatty acids as a source of energy in the mitochondria. For example, the inhibitor may inhibit the breakdown of intermediates such as butyryl CoA, glutaryl CoA, or isovaleryl CoA. In one embodiment, the inhibitor is a non-hydrolyzable analog of carnitine.

2,4-dienoyl-CoA reductase is an enzyme that catalyzes reduction reactions involved in the metabolism of polyunsaturated fatty acids. The fatty acid may be a substrate for the 2,4-dienoyl-CoA reductase within the mitochondria. In some cases, fatty acids may be transported into the mitochondria through uncoupling proteins. Additionally, the uncoupling protein may increase the mitochondrial metabolism to increase the throughput of beta-oxidation to increase the availability of the substrate.

2,4-dienoyl-CoA isomerase is an enzyme that catalyzes isomerization of certain fatty acids. One step in the metabolism of certain polyunsaturated fatty acids may be protective against reactive oxygen intermediates. Thus, by generating substrates and antagonists for the activity of 2,4-dienoyl-CoA isomerase, the production of reactive oxygen intermediates may be enhanced and/or reduced. This, in turn, may affect certain disease states, such as cancer.

It is to be understood that, as used herein, the moiety having the functionality of the oxirane carboxylic acid compound is also useful for altering cellular production of reactive oxygen within a cell. For example, by altering the ability of a cell to metabolize a fatty acid, the ability of the cell to produce reactive oxygen may also be affected since one pathway for a cell to produce reactive oxygen intermediates ("ROI") is through the metabolism of fatty acids. Alteration of the production of reactive oxygen in a cell may be associated with changes in the immune profile of cells, i.e., how immune cells respond to the cell. Thus, in some cases, exposing a cell to, or removing a cell from, a fatty acid metabolism inhibitor can affect the production of reactive oxygen. The alteration of the production of reactive oxygen may be useful in treating cancer and/or enhancing wound healing, as the alteration of the immune profile of cells within the cancer site or the wound may stimulate the immune system and/or other wound-healing processes.

The alteration of the production of reactive oxygen may also be useful in enhancing wound healing, as the alteration of the immune profile of cells within the wound may stimulate the wound-healing processes.

Preferred oxirane carboxylic acid compounds or moieties are derived from, or synthesized to function as, oxirane carboxylic acid compounds having the structure:

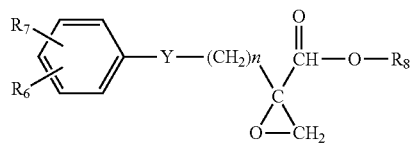

where $R_6$ and $R_7$ each represent a hydrogen atom, a halogen atom, a 1-4 carbon atom alkyl group, a 1-4 carbon atom alkoxy group, a nitro group or a trifluoromethyl group, $R_8$ represents a hydrogen atom or a 1-4 carbon atom alkyl group, Y represents $(CH_2)_k$ where k is from 2 to 8, 7 or the grouping —O—$(CH_2)_m$—, m is 0 or a whole number from 1 to 4, n is a whole number from 2 to 8 wherein the sum of m and n is a whole number from 2 to 8. More preferred are oxirane carboxylic acid compounds wherein $R_6$ is a halogen atom, $R_7$ is a hydrogen atom, m is 0, and n is 6, and more particularly where $R_8$ is an ethyl group. Most particularly preferred is etomoxir, i.e., 2-(6-(4-chlorophenoxy)-hexyl)-oxirane-2-carboxylic acid ethyl ester.

As used herein, the term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine, fluorine and chlorine, chlorine and bromine, or a single type of halogen atom.

Examples of such oxirane carboxylic acid compounds are: 2-(6-(4-chlorophenoxy)-hexyl)-oxirane-2-carboxylic acid ethyl ester, 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts. It is most particularly preferred to use etomoxir, i.e., 2-(6-(4-chlorophenoxy)-hexyl)-oxirane-2-carboxylic acid ethyl ester.

Some of the above oxirane carboxylic acid compounds are commercially available compounds, are derived from commercially available compounds, or are synthesized de novo using routine chemical synthetic procedures known to those of ordinary skill in the art and/or described herein.

In some embodiments of the invention, the fatty acid metabolism inhibitor, or the moiety functioning as a fatty acid metabolism inhibitor, may include homologs, analogs, derivatives, enantiomers and/or functionally equivalent compositions thereof and/or agents able to alter cellular production of reactive oxygen described herein. "Functionally equivalent" also refers to compositions capable of treatment of a subject that is wounded or exhibits symptoms of cancer (or other conditions described herein), a subject susceptible to or otherwise at increased risk for cancer, or a subject not exhibiting symptoms of cancer, but for whom it is desired to decrease the risk of cancer (e.g., a vaccination or a prophylactic treatment), etc. Homologs, analogs, derivatives, enantiomers and/or functionally equivalent compositions that are about as effective or more effective than the parent compound are also intended for use in the systems and methods of the invention. The synthesis of such compositions may be accomplished through typical chemical modification methods such as those routinely practiced by those of ordinary skill in the art.

In still another set of embodiments, the invention encompasses the use of antisense oligonucleotides that selectively bind to regions encoding enzymes present within the fatty acid metabolism pathway, such as 2,4-dienoyl-CoA reductase or 2,4-dienoyl-CoA isomerase. Thus, a fatty acid metabolism inhibitor, or a moiety functioning as a fatty acid metabolism inhibitor, in one embodiment, is an antisense oligonucleotide.

The fatty acid metabolism inhibitor, or moiety functioning as a fatty acid metabolism inhibitor, in yet another set of embodiments, includes a dominant negative plasma membrane polypeptide. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., *Molecular Cloning: A Laboratory Manual*, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

Preferred hypoglycin A compounds, or bifunctional compounds of this invention have a moiety that is derived from, or synthesized to function as, hypoglycin A, which has the structure:

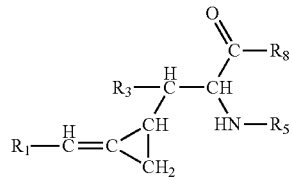

Where $R_1$, $R_3$, and $R_5$ each represent a hydrogen atom, a 1-4 carbon atom alkyl group, a 1-4 carbon atom alkoxy group, a nitro group, or a trifluoromethyl group, and $R_8$ is as given above.

Hypoglycin A itself has the structure:

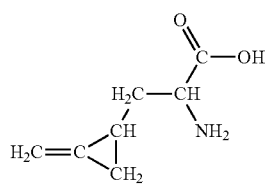

Bifunctional Compounds

Preferably, the invention provides bifunctional compounds that link a moiety having the functionality of an oxirane carboxylic acid compound to a moiety having the functionality of hypoglycin or a hypoglycin A derivative. Most preferred are bifunctional compounds that link a moiety having the functionality of etomoxir to a moiety having the functionality of hypoglycin A. Referring to FIGS. 1-4, generic forms of twelve bifunctional compounds (I) to (XII), are shown, and respective specific preferred bifunctional compounds (XIII) to (XXVII) are shown in FIGS. 5-9. Each will be referred to in more detail in the following examples, where $R_1$, $R_2$, $R_3$, $R_4$, and $R_5$ represents a hydroxyl group, a halogen atom, a thiol group, or CO—$R_9$ where $R_9$ represents an alkyl group of from 1 to 20 carbon atoms, $R_6$ and $R_7$ each represent a hydrogen atom, a halogen atom, a 1-4 carbon atom alkyl group, a 1-4 carbon atom alkoxy group, a nitro group or a trifluoromethyl group, $R_8$ represents a hydrogen atom or a 1-4 carbon atom alkyl group, Y represents $(CH_2)_k$ where k is from 2 to 8, 7 or the grouping —O—$(CH_2)_m$—, m is 0 or a whole number from 1 to 4, n is a whole number from 2 to 8 wherein the sum of m and n is a whole number from 2 to 8, and Z represents O, S or the grouping $(CH_2)_p$—O—$(CH_2)_q$ or $(CH_2)_p$—S—$(CH_2)_q$, and p and q are each 0 or a whole number from 1 to 4.

EXAMPLE 1

One can use in the invention, to treat MDR tumors, the bifunctional compound (I) of FIG. 1, having the structure:

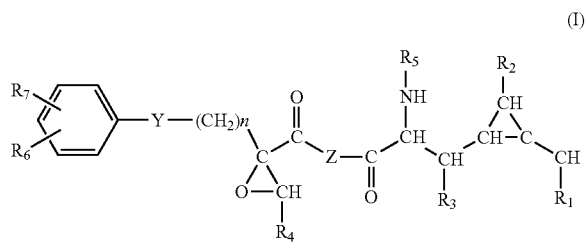

Figure 5:
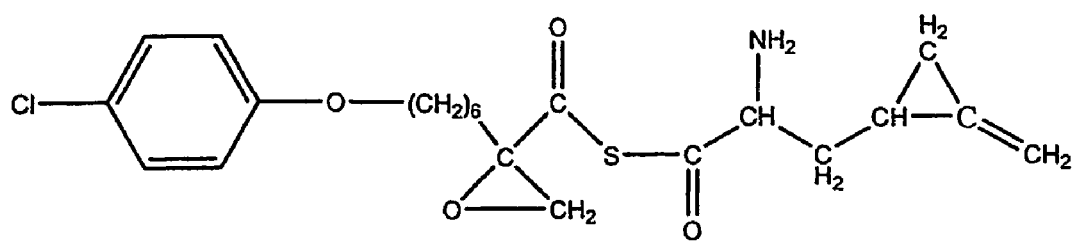
FIG. 5 shows specific chemical structures (XIII), (XIV), and (XV) of a set of bifunctional compounds of this invention within the generic structures, respectively (I), (II), and (III), of FIG. 1.
Figure 5:
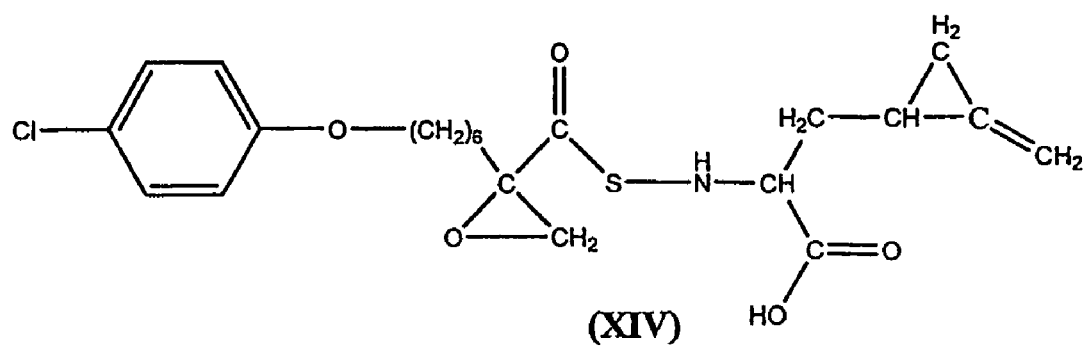
Figure 5:
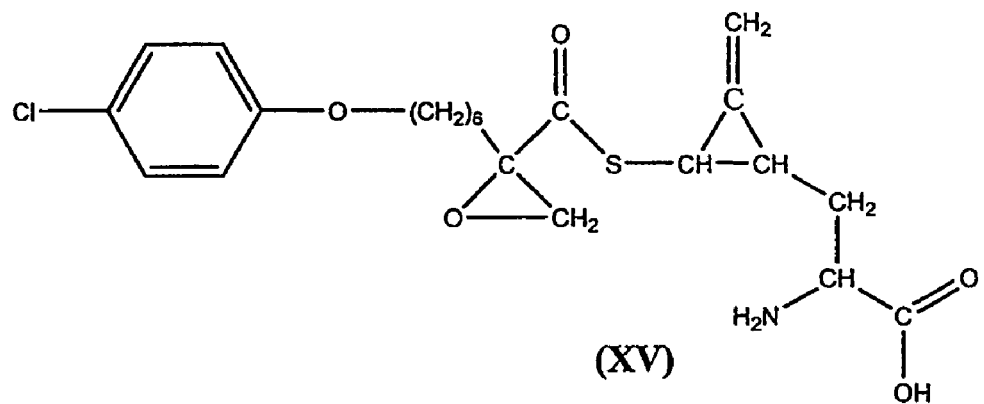

A preferred specific example of bifunctional compound (I) is shown in FIG. 5 as compound (XIII), having the structure:

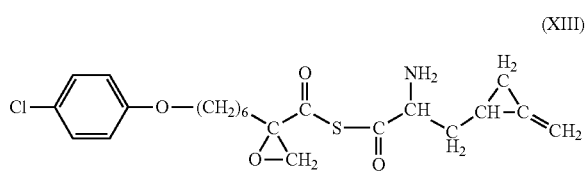

EXAMPLE 2

One can use in the invention, to treat MDR tumors, the bifunctional compound (II) of FIG. 1, having the structure:

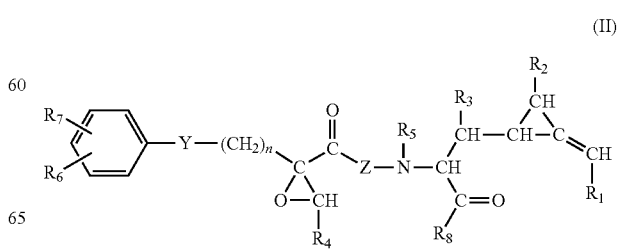

A preferred specific example of bifunctional compound (II) is shown in FIG. 5 as compound (XIV), having the structure:

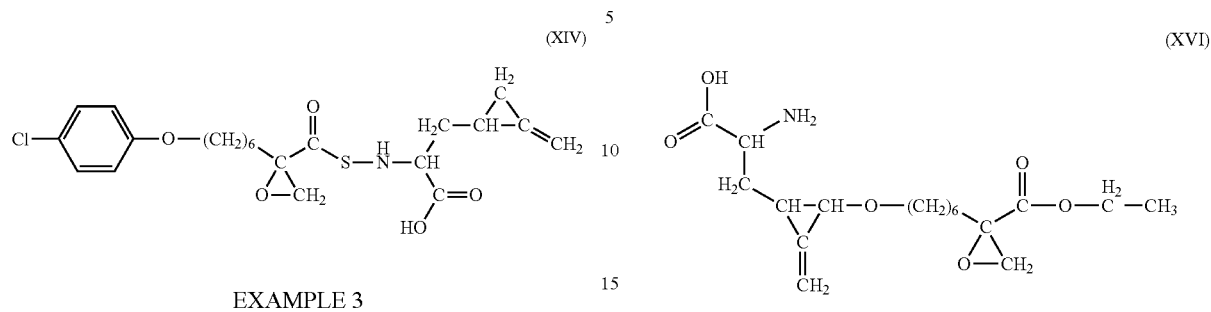

(XIV)

EXAMPLE 3

Figure 2:
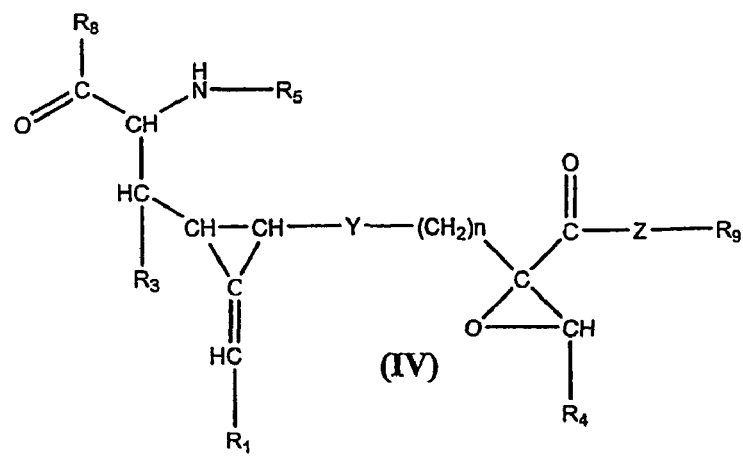
FIG. 2 shows generic chemical structures (IV), (V), and (VI) of a second set of three embodiments of bifunctional compounds of this invention.
Figure 2:
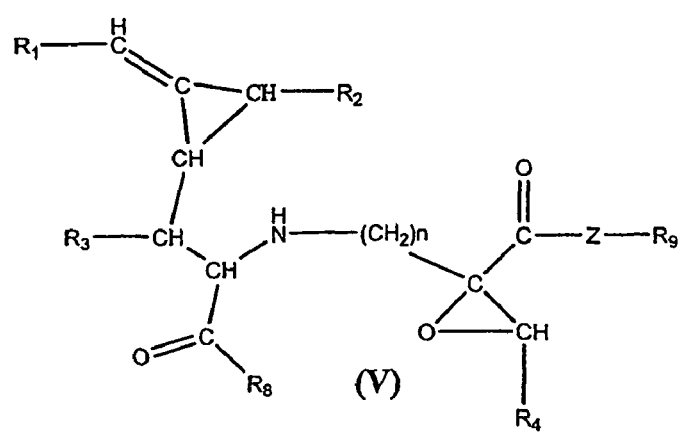
Figure 2:
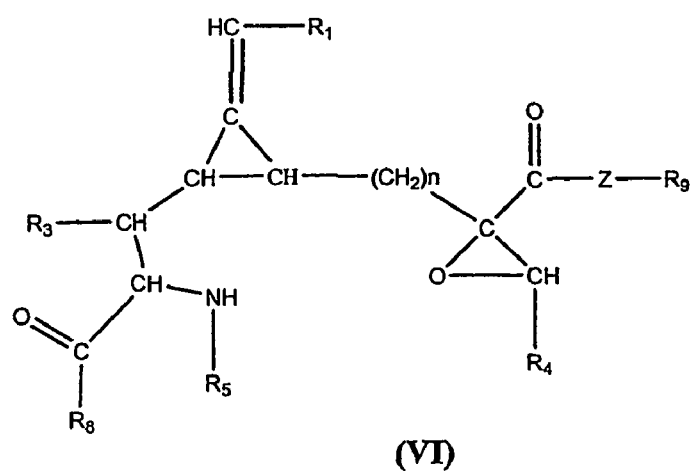

One can use in the invention, to treat MDR tumors, the bifunctional compound (III) of FIG. 2, having the structure:

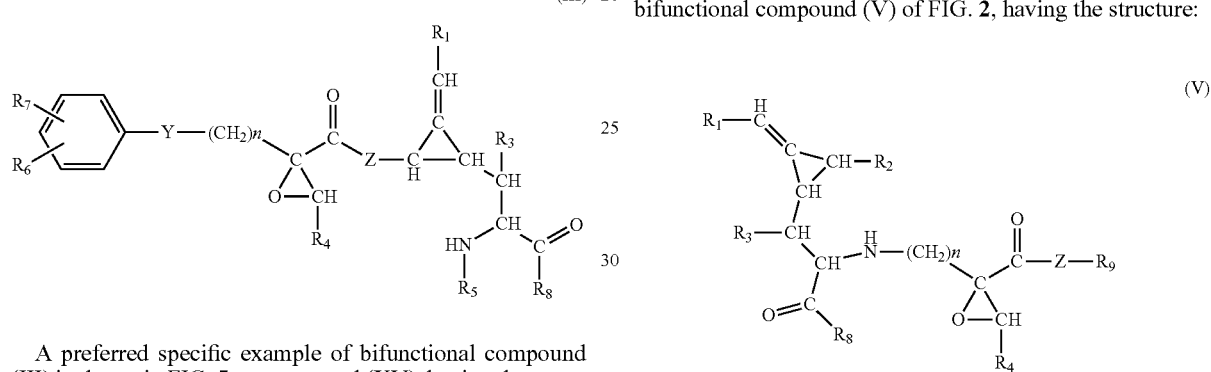

(III)

A preferred specific example of bifunctional compound (III) is shown in FIG. 5 as compound (XV), having the structure:

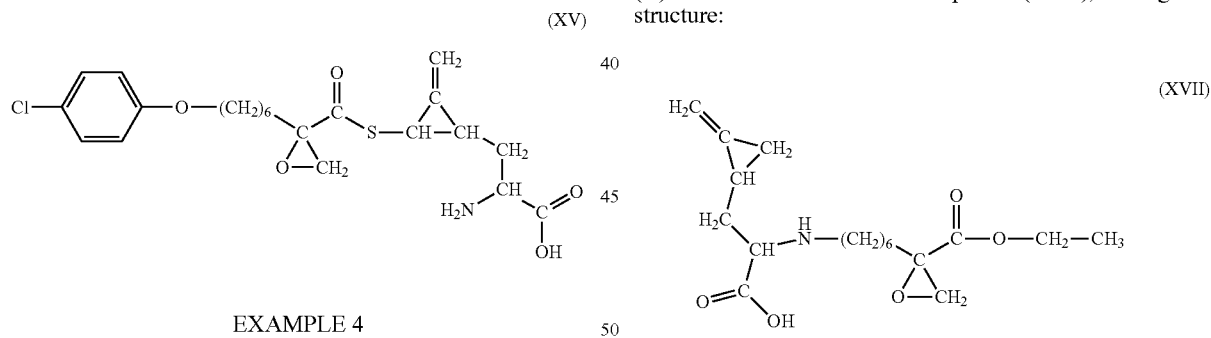

(XV)

EXAMPLE 4

One can use in the invention, to treat MDR tumors, the bifunctional compound (IV) of FIG. 2, having the structure:

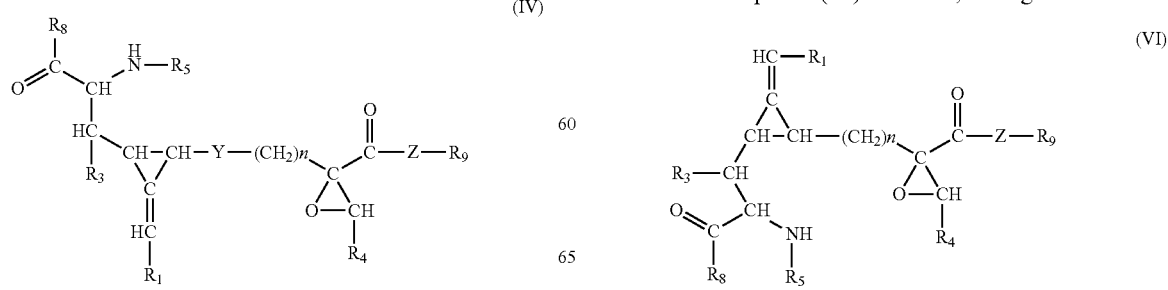

(IV)

Figure 6:
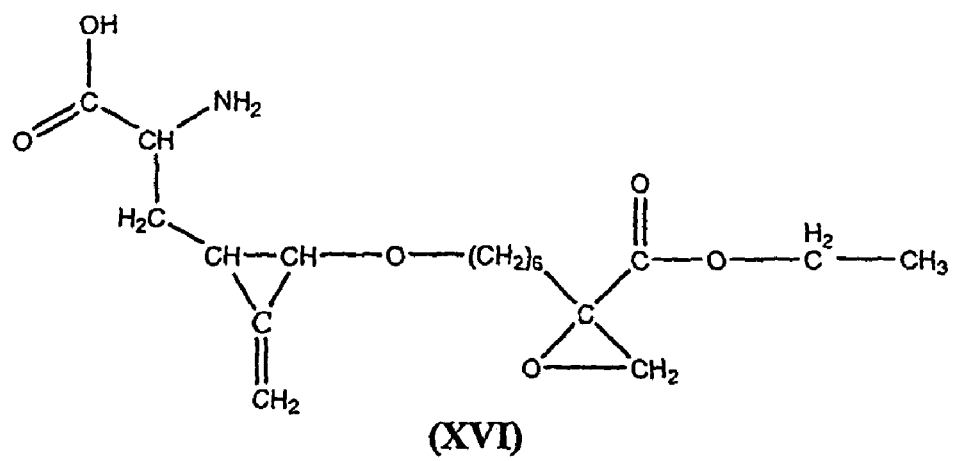
FIG. 6 shows specific chemical structures (XVI), (XVII), and (XVIII) of a set of bifunctional compounds of this invention within the generic structures, respectively (IV), (V), and (VI), of FIG. 2.
Figure 6:
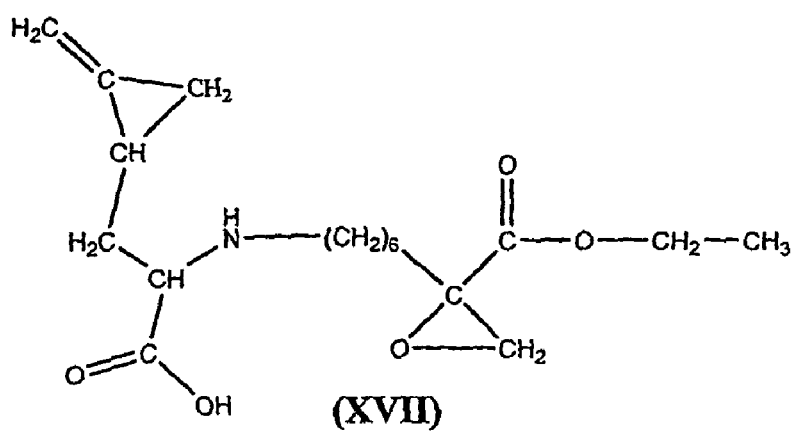
Figure 6:
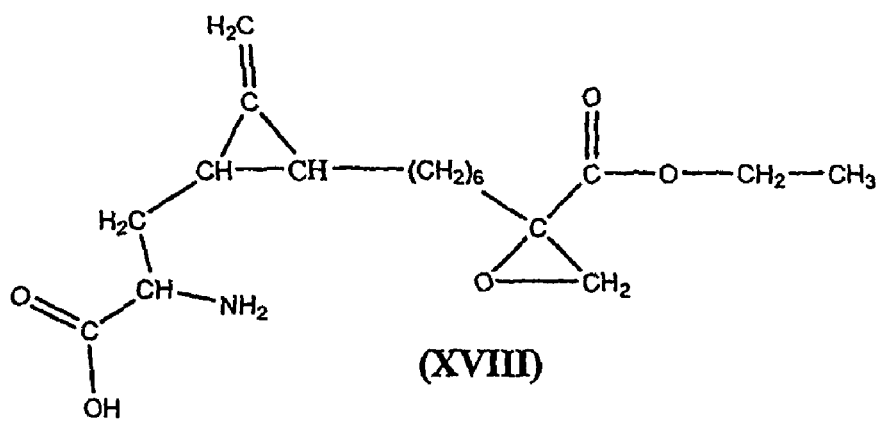

A preferred specific example of bifunctional compound (IV) is shown in FIG. 6 as compound (XVI), having the structure:

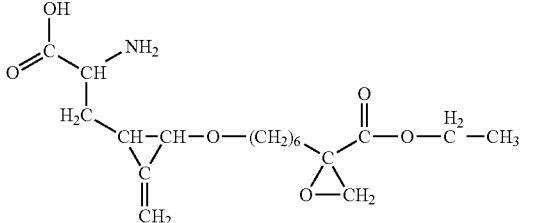

(XVI)

EXAMPLE 5

One can use in the invention, to treat MDR tumors, the bifunctional compound (V) of FIG. 2, having the structure:

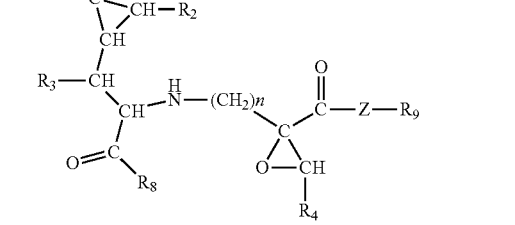

(V)

A preferred specific example of bifunctional compound (V) is shown in FIG. 6 as compound (XVII), having the structure:

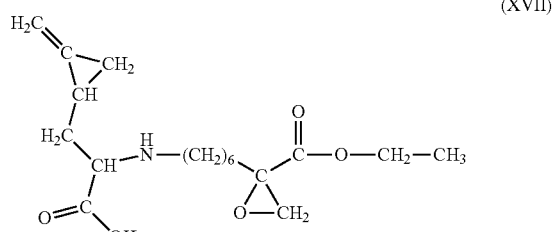

(XVII)

EXAMPLE 6

One can use in the invention, to treat MDR tumors, the bifunctional compound (VI) of FIG. 2, having the structure:

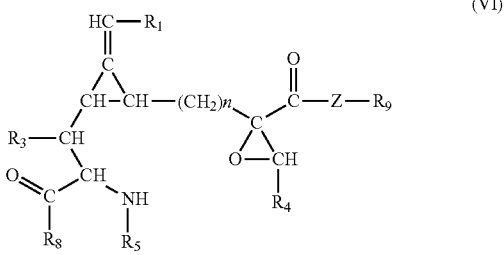

(VI)

A preferred specific example of bifunctional compound (VI) is shown in FIG. 6 as compound (XVIII), having the structure:

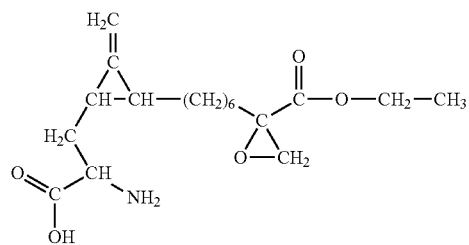

(XVIII)

EXAMPLE 7

Figure 3:
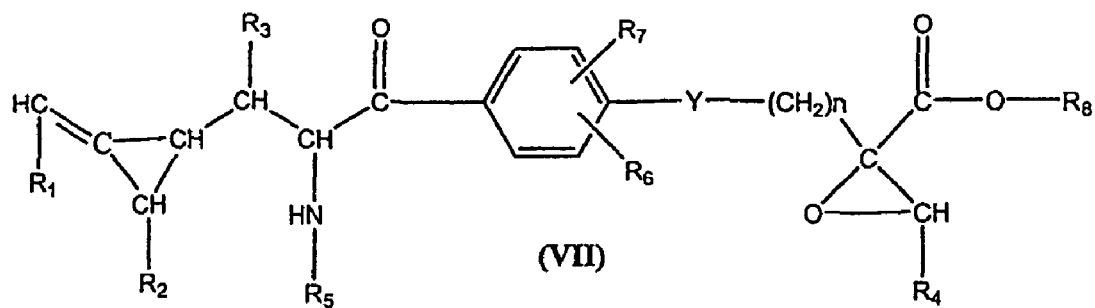
FIG. 3 shows generic chemical structures (VII), (VIII), and (IX) of a third set of three embodiments of bifunctional compounds of this invention.
Figure 3:
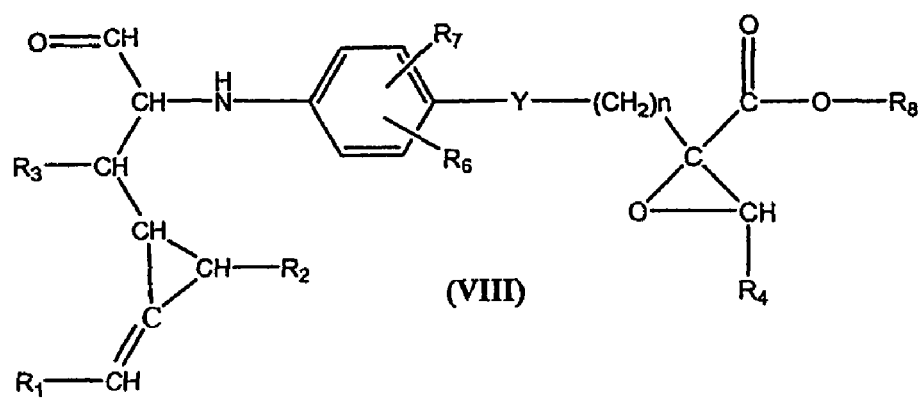
Figure 3:
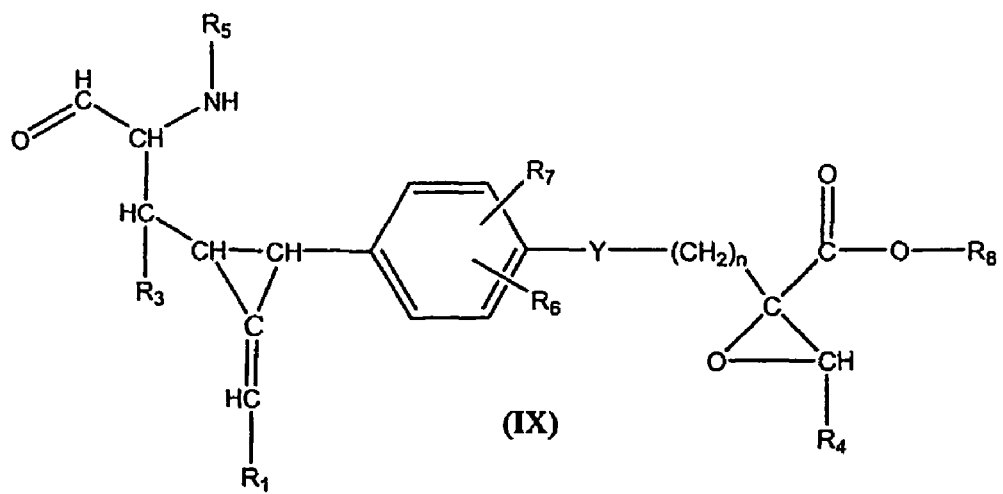

One can use in the invention, to treat MDR tumors, the bifunctional compound (VII) of FIG. 3, having the structure:

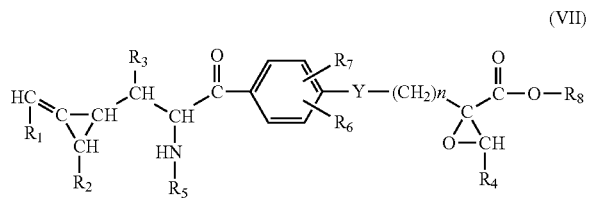

(VII)

Figure 7:
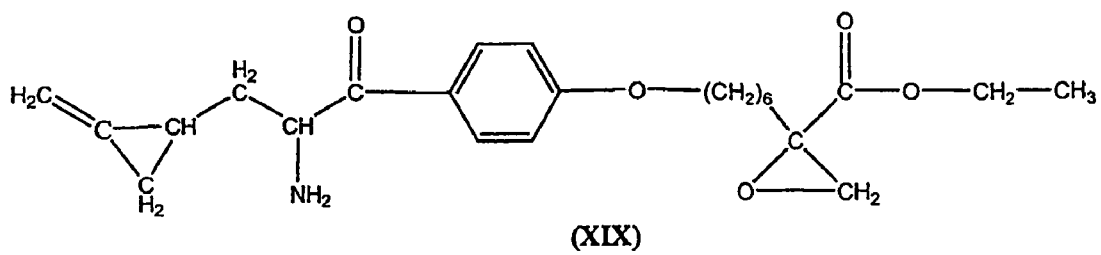
FIG. 7 shows specific chemical structures (XIX), (XX), and (XXI) of a set of bifunctional compounds of this invention within the generic structures, respectively (VII), (VIII), and (IX), of FIG. 3.
Figure 7:
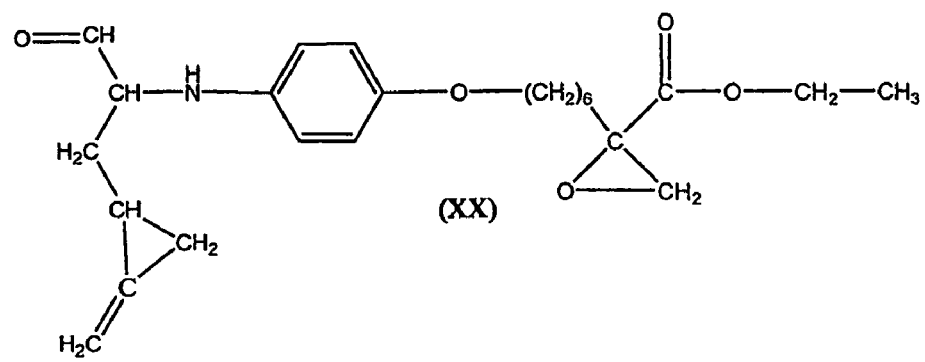
Figure 7:
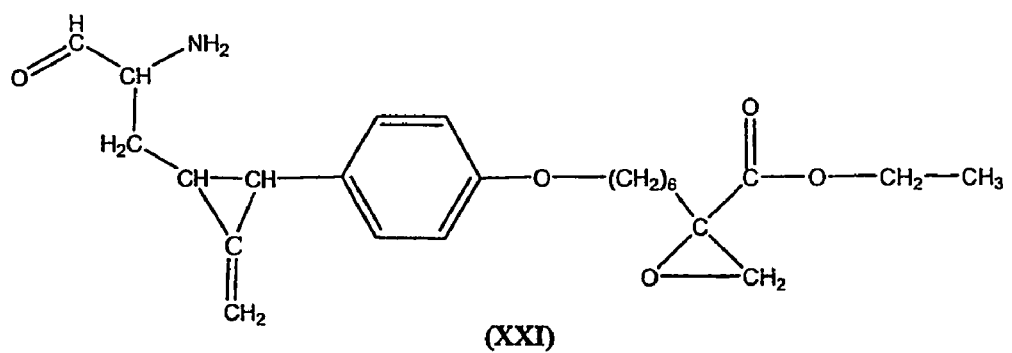

A preferred specific example of bifunctional compound (VII) is shown in FIG. 7 as compound (XIX), having the structure:

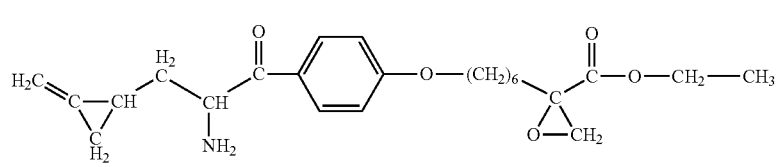

(XIX)

EXAMPLE 8

One can use in the invention, to treat MDR tumors, the bifunctional compound (VIII) of FIG. 3, having the structure:

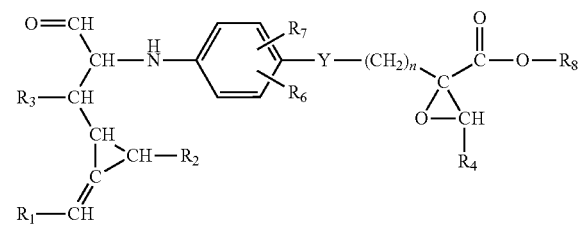

(VIII)

A preferred specific example of bifunctional compound (VIII) is shown in FIG. 7 as compound (XX), having the structure:

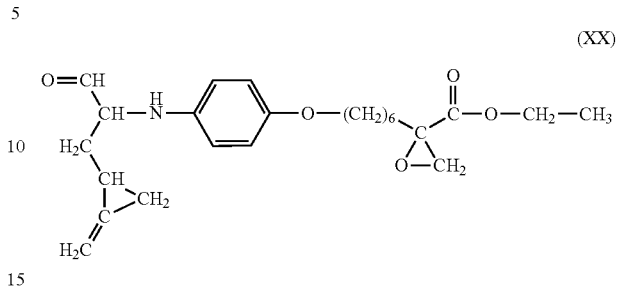

(XX)

EXAMPLE 9

One can use in the invention, to treat MDR tumors, the bifunctional compound (IX) of FIG. 3, having the structure:

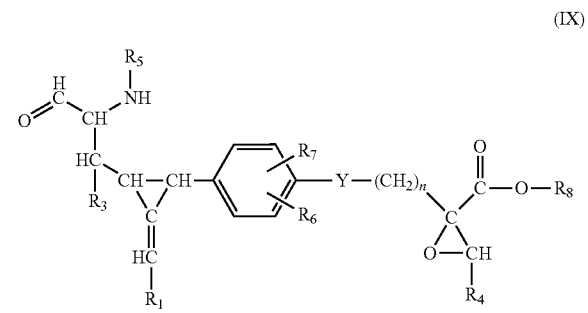

(IX)

A preferred specific example of bifunctional compound (XXI) is shown in FIG. 6 as compound (XVII), having the structure:

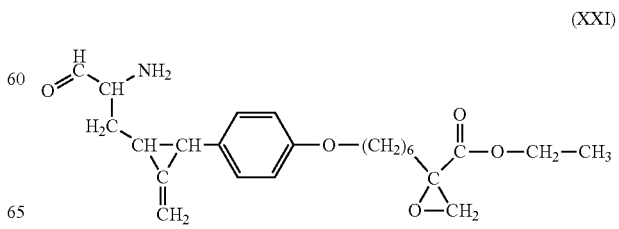

(XXI)

EXAMPLE 10

Figure 4:
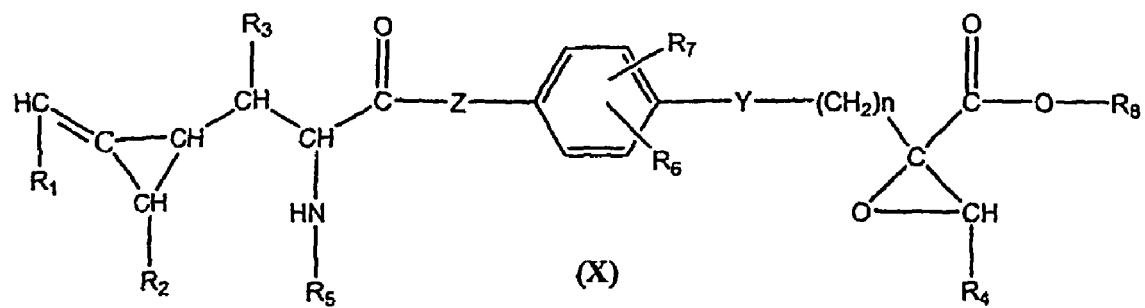
FIG. 4 shows generic chemical structures (X), (XI), and (XII) of a fourth set of three embodiments of bifunctional compounds of this invention.
Figure 4:
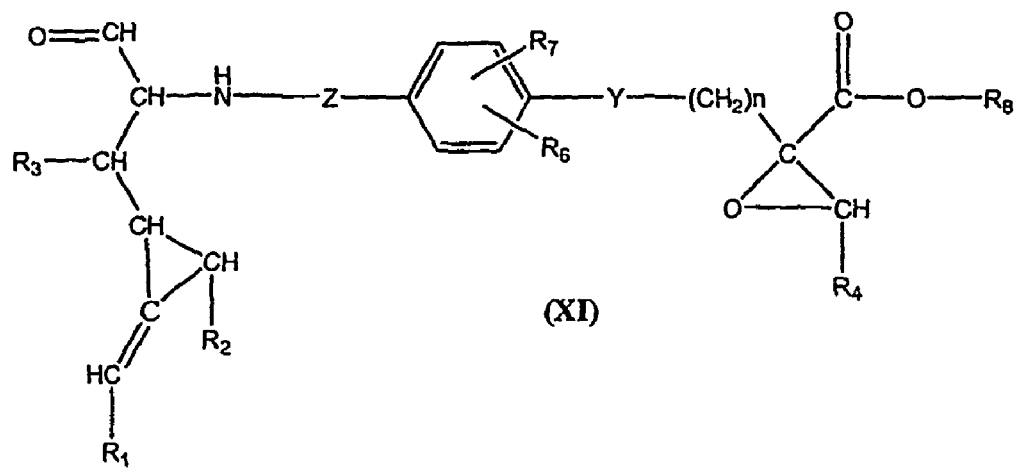
Figure 4:
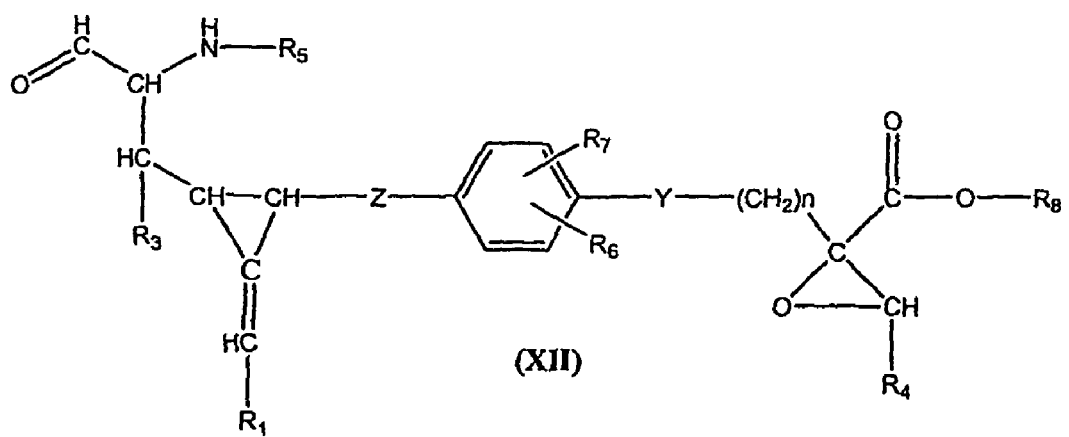

One can use in the invention, to treat MDR tumors, the bifunctional compound (X) of FIG. 4, having the structure:

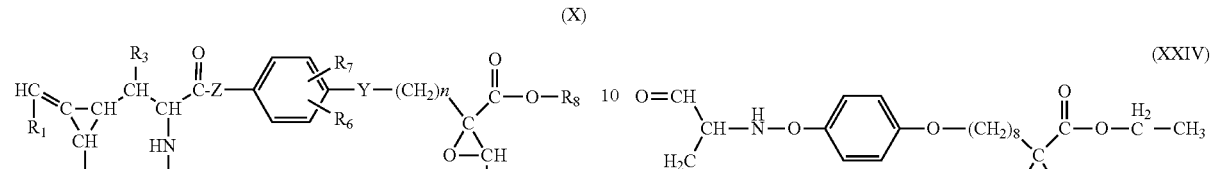
(X)

Figure 8:
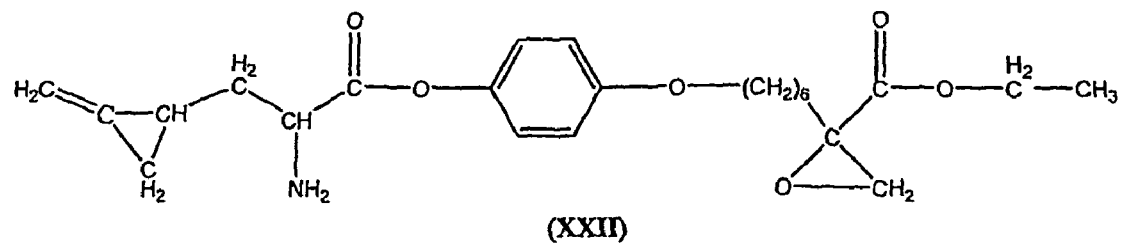
FIG. 8 shows specific chemical structures (XXII), (XXIII), and (XIV) of a set of bifunctional compounds of this invention within the generic structures, respectively (X), (X), and (XI), of FIG. 4.
Figure 8:
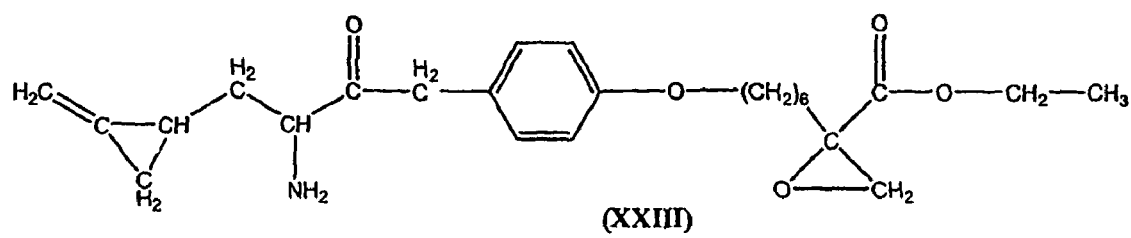
Figure 8:
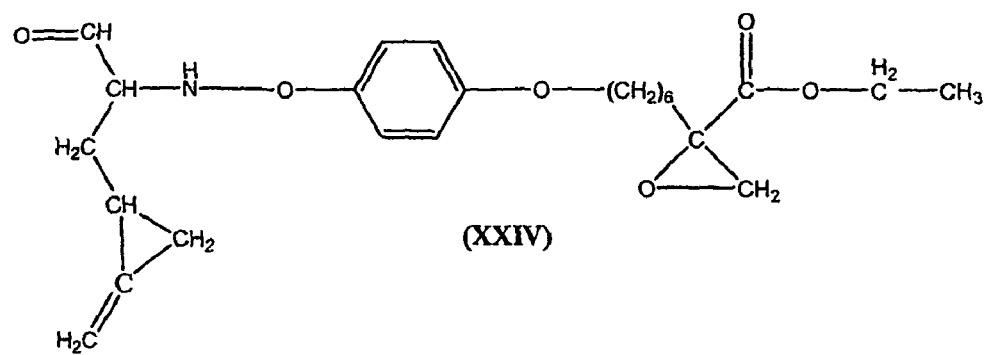

A preferred specific example of bifunctional compound (X) is shown in FIG. 8 as compound (XXII), having the structure:

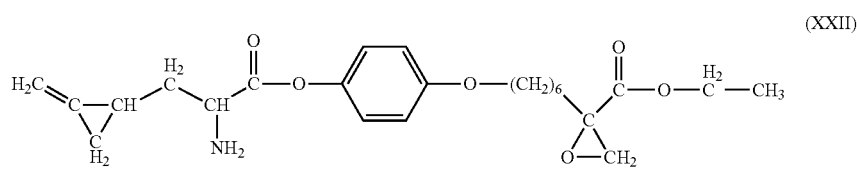
(XXII)

Another preferred specific example of bifunctional compound (X) is shown in FIG. 8 as compound (XXIII), having the structure:

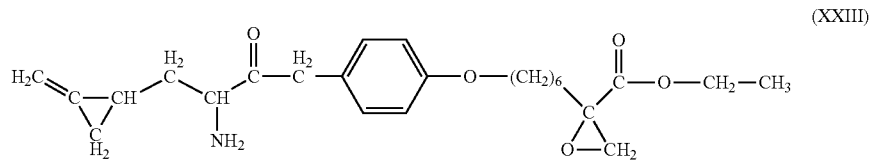
(XXIII)

EXAMPLE 11

One can use in the invention, to treat MDR tumors, the bifunctional compound (XI) of FIG. 4, having the structure:

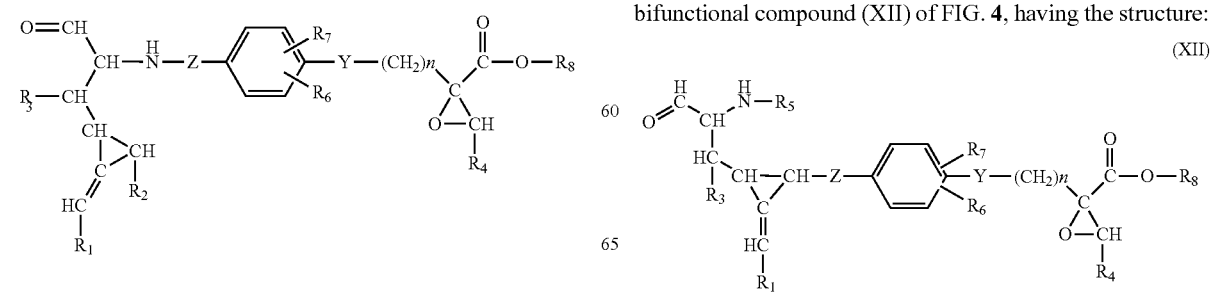
(XI)

A preferred specific example of bifunctional compound (XI) is shown in FIG. 8 as compound (XXIV), having the structure:

(XXIV)

Figure 9:
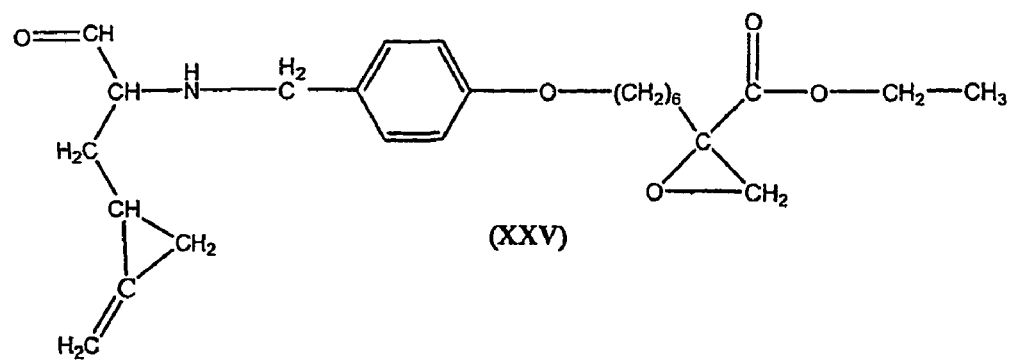
FIG. 9 shows specific chemical structures (XXV), (XXVI), and (XXVII) of a set of bifunctional compounds of this invention within the generic structures, respectively (XI), (XII), and (XII), of FIG. 4.
Figure 9:
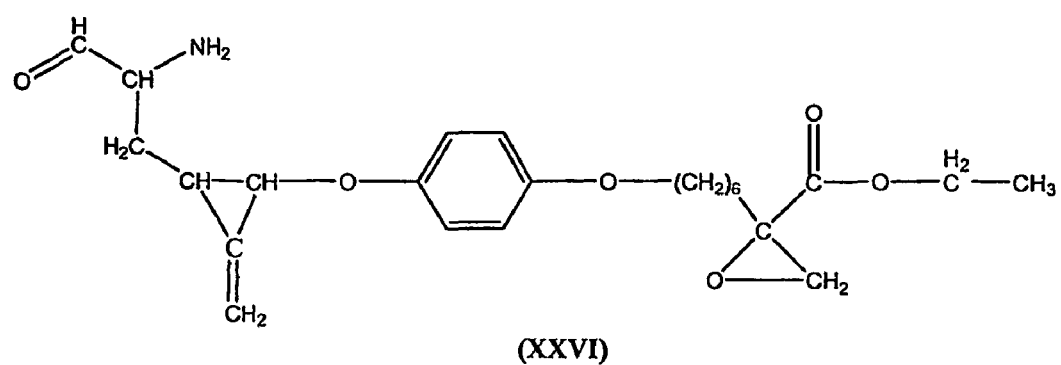
Figure 9:
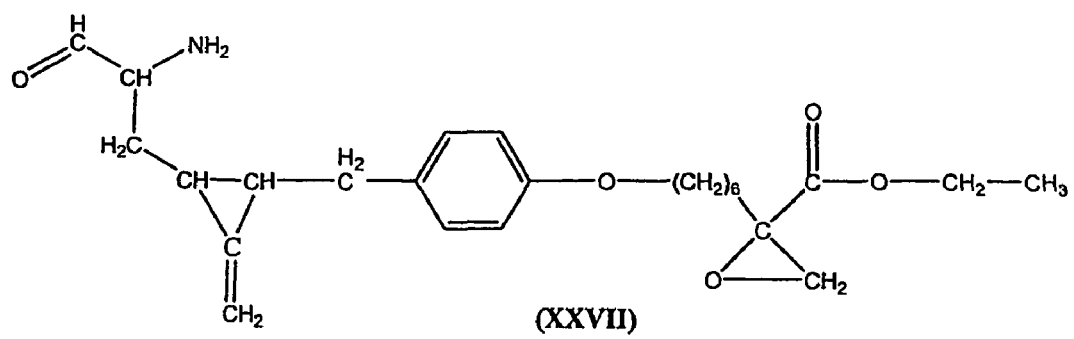

Another preferred specific example of bifunctional compound (XI) is shown in FIG. 9 as compound (XXV), having the structure:

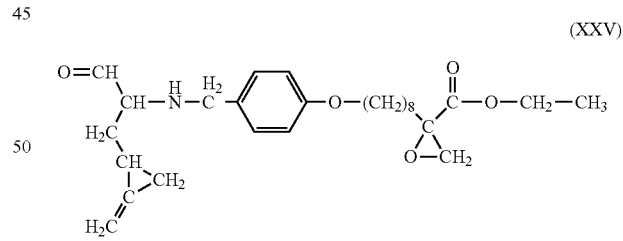
(XXV)

EXAMPLE 12

One can use in the invention, to treat MDR tumors, the bifunctional compound (XII) of FIG. 4, having the structure:

(XII)

A preferred specific example of bifunctional compound (XII) is shown in FIG. 9 as compound (XXVI), having the structure:

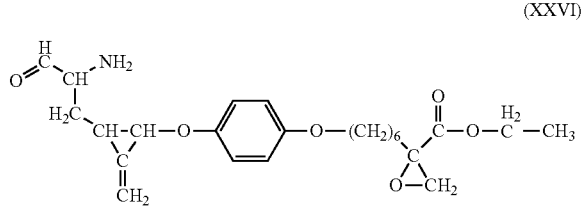

(XXVI)

Another preferred specific example of bifunctional compound (XII) is shown in FIG. 9 as compound (XXVII), having the structure:

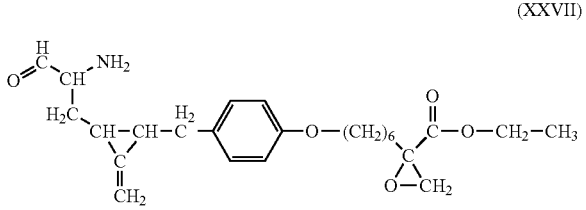

(XXVII)

In General

In one aspect, the systems and methods of the invention are useful in treating cancers, tumors, and other conditions involving rapidly dividing cell populations that are typically uncontrolled. A "rapidly dividing cell," as used herein, is a cell that is undergoing mitotic growth. Such cells are well known in the art and include, but are not limited to, tumor cells, cancer cells, lymphocytes (T cells or B cells), bacteria, and pancreatic beta (β) cells. The systems and methods are useful for inducing cell death in many types of mammalian cells, including in tumor cells. A "tumor cell," as used herein, is a cell that is undergoing unwanted mitotic proliferation. A tumor cell, when used in the in vitro aspects of the invention, can be isolated from a tumor within a subject, or may be part of an established cell line.

As used herein, the term "cell death" is used to refer to either of the processes of apoptosis or cell lysis. In both apoptosis and cell lysis, the cell dies, but the processes occur through different mechanisms and/or different metabolic states of the cell. Apoptosis is a process of cell death in which the cell undergoes shrinkage and fragmentation, followed by phagocytosis of the cell fragments. Apoptosis is well known in the art and can be assessed by any art-recognized method. For example, apoptosis can easily be determined using flow cytometry, which is able to distinguish between live and dead cells.

A tumor cell in a subject may be part of any type of cancer. Cancers include, but are not limited to, biliary tract cancer, bladder cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In general, an effective amount of a composition for treating a cancer will be that amount necessary to inhibit mammalian cancer cell proliferation in situ. Those of ordinary skill in the art are well schooled in the art of evaluating effective amounts of anti-cancer agents.

In one set of embodiments, the invention includes a method of treating a subject susceptible to or exhibiting symptoms of cancer. In some cases, the cancer is drug-resistant or multi-drug resistant. As used herein, a "drug-resistant cancer" is a cancer that is resistant to conventional commonly known cancer therapies. Examples of conventional cancer therapies include treatment of the cancer with agents such as methotrexate, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action. In some cases, the subject is not otherwise indicated for treatment with the inhibitor, for example, the subject is not indicated for obesity treatment.

In one aspect, any of the systems and methods of the invention described herein can be used in conjunction with one or more other forms of cancer treatment, for example, in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Aspects of cancer treatment that may vary include, but are not limited to, dosages, timing of administration or duration or therapy, and the cancer treatment can vary in dosage, timing, or duration. Another treatment for cancer is surgery, which can be utilized either alone or in combination with any of the previously treatment methods. One of ordinary skill in the medical arts can determine an appropriate treatment for a subject.

In one embodiment, the cancer treatment may include treatment with an anti-cancer agent or drug, for example, a conventionally-known anti-cancer agent or drug. Examples of suitable anti-cancer agents and drugs include, but are not limited to, 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplant, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalFasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

In one set of embodiments, cells may be removed from a tumor (e.g., a tumor from a subject, a tumor growing in vitro, etc.) and exposed in some Fashion to the systems and methods described herein. After suitable exposure, the exposed cells may be introduced into a subject. In one embodiment, exposure of the cells may alter the immunological profile of the tumor cells in some Fashion, for example, such that a subject's immune system is able to recognize the tumor cells. The subject's immune system, after interacting with the exposed cells, may then be able to recognize tumors present within the subject, thus causing the cancer to decrease. If the subject has a tumor, the cells may be injected into the tumor, proximate the tumor, and/or systemically or locally delivered in a region of the body away from the tumor. In some cases, a tumor may be removed from a subject, then the exposed cells may be inserted, e.g., into the cavity created upon removal of the tumor, or to another site within the body. Optionally, other cancer treatment methods, such as radiation or exposure to conventional anti-cancer agents, may also be used in conjunction with these methods. In some cases, the subject may not have a cancer or tumor, but the cells may be injected to stimulate the immune system to produce antibodies against future cancers and/or other uncontrolled cellular growths, i.e., "immunizing" the subject from cancer and/or other uncontrolled cellular growths.

In some the cancer cells are antigenic and can be targeted by the immune system. Thus, the combined administration of the systems and methods of the invention and cancer medicaments, particularly those which are classified as cancer immunotherapies, can be very useful for stimulating a specific immune response against a cancer antigen. A "cancer antigen" as used herein is a compound, such as a peptide, associated with a tumor or cancer cell surface, and which is capable of provoking an immune response when expressed on the surface of an antigen-presenting cell in the context of an MHC molecule. Cancer antigens, such as those present in cancer vaccines or those used to prepare cancer immunotherapies, can be prepared from crude cancer cell extracts, e.g., as described in Cohen, et al, *Cancer Research,* 54:1055, 1994, or by partially purifying the antigens, using recombinant technology, or de novo synthesis of known antigens. Cancer antigens can be used in the form of immunogenic portions of a particular antigen, or in some instances, a whole cell or a tumor mass can be used as the antigen. Such antigens can be isolated or prepared recombinantly or by any other means known in the art.

The systems and methods of the invention can be used in combination with immunotherapeutics in certain cases. The goal of immunotherapy is to augment a subject's immune response to an established tumor. One method of immunotherapy includes the use of adjuvants. Adjuvant substances derived from microorganisms, such as *bacillus Calmette-Guerin*, can heighten the immune response and enhance resistance to tumors in animals. Immunotherapeutic agents are often medicaments that derive from antibodies or antibody fragments that specifically bind to or otherwise recognize a cancer antigen. Binding of such agents can promote an immune response, such as an antigen-specific immune response. Antibody-based immunotherapies may function by binding to the cell surface of a cancer cell, which can stimulate the endogenous immune system to attack the cancer cell.

As used herein, a "cancer antigen" is broadly defined as an antigen expressed by a cancer cell. The antigen can be expressed at the cell surface of the cancer cell. In many cases, the antigen is one that is not expressed by normal cells, or at least not expressed at the same level or concentration as in cancer cells. As examples, some cancer antigens are normally silent (i.e., not expressed) in normal cells, some are expressed only at certain stages of differentiation, and others are only temporally expressed (such as embryonic and fetal antigens). Other cancer antigens are encoded by mutant cellular genes, such as oncogenes (e.g., activated ras oncogene), suppressor genes (e.g., mutant p53), fusion proteins resulting from internal deletions or chromosomal translocations, or the like. Still other cancer antigens can be encoded by viral genes, such as those carried on RNA and DNA tumor viruses. The differential expression of cancer antigens in normal and cancer cells can be exploited in order to target cancer cells in some cases. As used herein, the terms "cancer antigen" and "tumor antigen" are used interchangeably.

The theory of immune surveillance is that a prime function of the immune system is to detect and eliminate neoplastic cells before a tumor forms. A basic principle of this theory is that cancer cells are antigenically different from normal cells and thus can elicit immune reactions similar to those that cause rejection of immunologically incompatible allografts. Studies have confirmed that tumor cells differ, qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen-dependent, nor MHC-restricted, once activated. Activated macrophages are thought to decrease the growth rate of the tumors they infiltrate. In vitro assays have identified other immune mechanisms such as antibody-dependent, cell-mediated cytotoxic reactions, and lysis by antibody plus complement. However, these immune effector mechanisms are thought to be less important in vivo than the function of NK, CTLs, LAK, and macrophages in vivo (for a review, see Piessens, "Tumor Immunology," in *Scientific American Medicine*, Vol. 2, Scientific American Books, p. 1-13, 1996).

In one embodiment, the immunotherapeutic agent may function as a delivery system for the specific targeting of toxic substances to cancer cells. For example, the agent may be conjugated to toxins such as ricin (e.g., from castor beans), calicheamicin, maytansinoids, radioactive isotopes such as iodine-131 and yttrium-90, chemotherapeutic agents, and/or to biological response modifiers. In this way, the toxic substances can be concentrated in the region of the cancer and non-specific toxicity to normal cells can be minimized.

In another embodiment, the immunotherapeutic agent may be directed towards the binding of vasculature, such as those that bind to endothelial cells. This is because solid tumors are generally dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

In another set of embodiments, the combined administration of the systems and methods of the invention and an apoptotic chemotherapeutic agent may be used. An "apoptotic chemotherapeutic agent," as used herein, includes molecules that function by a variety of mechanisms to induce apoptosis in rapidly dividing cells. Apoptotic chemotherapeutic agents are a class of chemotherapeutic agents that are well known to those of ordinary skill in the art. Chemotherapeutic agents include those agents disclosed in Chapter 52, "Antineoplastic Agents" (Paul Calabresi and Bruce A. Chabner), and the introduction thereto, p. 1202-1263, of Goodman and Gilman's *The Pharmacological Basis of Therapeutics*, Eighth Edition, McGraw-Hill, Inc. Health Professions Division, 1990, incorporated herein by reference. Suitable chemotherapeutic agents may have various mechanisms of action. Classes of suitable chemotherapeutic agents include, but are not limited to: (a) alkylating agents, such as nitrogen mustard (e.g. mechlorethamine, cylophosphamide, ifosfamide, melphalan, chlorambucil), ethylenimines and methylmelamines (e.g. hexamethylmelamine, thiotepa), alkyl sulfonates (e.g. busulfan), nitrosoureas (e.g. carmustine, which is also known as BCNU, lomustine which is also known as CCNU, semustine, which is also known as methyl-CCNU, chlorozoticin, streptozocin), and triazines (e.g. dicarbazine, which is also known as DTIC), (b) antimetabolites, such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin), (c) natural products, such as the vinca alkaloids (e.g. vinblastine, vincristine), epipodophylotoxins (e.g. etoposide, teniposide), antibiotics (e.g. dactinomycin, which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (e.g. L-asparaginase), and biological response modifiers (e.g. interferon alfa), (d) miscellaneous agents, such as the platinum coordination complexes (e.g. cisplatin, carboplatin), substituted ureas (e.g. hydroxyurea), methylhydiazine derivatives (e.g. procarbazine), adreocortical suppressants (e.g. mitotane, aminoglutethimide) taxol, (e) hormones and antagonists, such as adrenocorticosteroids (e.g. prednisone or the like), progestins (e.g. hydroxyprogesterone caproate, medroxyprogesterone acetate, megestrol acetate), estrogens (e.g. diethyestilbestrol, ethinyl estradiol, or the like), antiestrogens (e.g. tamoxifen), androgens (e.g. testosterone propionate, fluoxymesterone, or the like), antiandrogens (e.g. flutamide), and gonadotropin-releasing hormone analogs (e.g. leuprolide), and (f) DNA damaging compounds, such as adriamycin. The combined administration of the systems and methods of the invention and an apoptotic chemotherapeutic agent effective to inhibit growth of the tumor cell is that amount effective to induce apoptosis of the tumor cell in some cases.

In yet another set of embodiments, the systems and methods of the invention may be used in conjunction with a cancer vaccine. Cancer vaccines are medicaments that are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes that are capable of killing tumor cells. Cancer vaccines generally enhance the presentation of cancer antigens to both antigen-presenting cells (e.g., macrophages and dendritic cells) and/or to other immune cells such as T cells, B cells, and NK cells.

Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine, which is a preparation of cancer cells that have been removed from a subject, treated ex vivo and then reintroduced as whole cells in the subject. Lysates of tumor cells can also be used as cancer vaccines to elicit an immune response in certain cases. Another form of cancer vaccine is a peptide vaccine, which uses cancer-specific or cancer-associated small proteins to activate T cells. Cancer-associated proteins are proteins that are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine, which includes whole dendritic cells that have been exposed to a cancer antigen or a cancer-associated antigen in vitro. Lysates or membrane fractions of dendritic cells may also be used as cancer vaccines in some instances. Dendritic cell vaccines are able to activate antigen-presenting cells directly. Other non-limiting examples of cancer vaccines include ganglioside vaccines, heat-shock protein vaccines, viral and bacterial vaccines, and nucleic acid vaccines.

In some embodiments, cancer vaccines may be used along with adjuvants. Adjuvants are substances that activate the subject's immune system, and can be used as an adjunct therapy in any of the systems or methods of the invention. Adjuvants include, for example, alum, QS-Stimulon (Aquila), MF-59 (Chiron), Detox (Ribi), Optivax (Vaxcels) and LeIF (Corixa).

Other cancer vaccines take the form of dendritic cells that have been exposed to cancer antigens in vitro, have processed the antigens and are able to express the cancer antigens at their cell surface in the context of MHC molecules for effective antigen presentation to other immune system cells.

The invention, in still another aspect, is useful for treating other diseases associated with rapidly dividing cells, such as rheumatoid arthritis and scleroderma. Rheumatoid arthritis is associated in its early stages with the rapid division of synoviocytes. This process is referred to a pannus formation. The rapidly dividing cells produce a substance that kills osteocytes leading to the hardening of the tissue.

In another aspect, the systems and methods of the invention are useful in treating wounds in subjects. As used herein, the term "wound" is used to describe skin wounds as well as tissue wounds. A "skin wound" is defined herein as a break in the continuity of skin tissue that is caused by direct injury to the skin. Skin wounds are generally characterized by several classes including punctures, incisions, including those produced by surgical procedures, excisions, lacerations, abrasions, atrophic skin, or necrotic wounds and burns. The systems and methods of the invention are useful for enhancing the healing of all wounds of the skin.

A "tissue wound," as used herein, is a wound to an internal organ, such as a blood vessel, intestine, colon, etc. The systems and methods of the invention are useful for enhancing the wound healing process in tissue wounds, whether they arise naturally, or as the result of surgery. For instance, during the repair of arteries an artery may need to be sealed and wound healing promoted as quickly as possible. The systems and methods of the invention can speed up that process in many cases. The invention may also be particularly useful for the treatment of damaged tissue in the colon. In addition to promoting wound healing of the damaged colon, in some cases, the systems and methods of the invention can provide an antimicrobial effect.

The cells treated according to the present invention may be used to treat a wound. For example, ex vivo cells may be attached to a bandage or other substrate, and the substrate positioned over a wound, at least partially covering the wound. In some cases, the bandage or other substrate may be adhered to the subject, for example, through the use of adhesives. Suitable adhesives can be selected by those of ordinary skill in the art, some suitable adhesives are further described below.

The systems and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors-A and -B, osteoid-inducing factors, osteogenin and other bone growth factors, collagen growth factors, heparin-binding growth factor-1 or -2, and/or their biologically active derivatives. The compositions may also include antiseptics in some embodiments.

In another aspect, the systems and methods of the invention are useful for treating or preventing disorders associated with a specific antigenic immune response. Thus, in some embodiments of the invention, the methods are used to treat mammals at risk of, or afflicted with, autoimmune disease. Autoimmune disease is a disorder in which the host's immune response is defective and results in the production of a specific immune response against the individual's own antigens or components. In an autoimmune disease, an individual's own antibodies react with host tissue or in which immune effector T cells are autoreactive to endogenous self-peptides and cause destruction of tissue. It is well established that MHC class II alleles act as major genetic elements in susceptibility to a variety of autoimmune diseases. The structures recognized by T cells, the cells that cause autoimmunity, are complexes comprised of class II MHC molecules and antigenic peptides. When the T cells react with the host's class II MHC molecules-peptide complexes derived from a host's own gene products, autoimmune disease can result. If these class II MHC/peptide complexes are inhibited from being formed, the autoimmune response is reduced or suppressed, and thus is inhibited according to the invention. The peptide-antigen of autoimmune disorders are self-antigens. Any autoimmune disease in which class II MHC/peptide complexes play a role may be treated according to the methods of the present invention. Such autoimmune diseases include, but are not limited to, juvenile-onset diabetes (insulin-dependent), multiple sclerosis, pemphigus vulgaris, Graves's disease, myasthenia gravis, systemic lupus erythematosus (SLE), celiac disease rheumatoid arthritis, and Hashimoto's thyroiditis. The invention includes a method for determining an individual's susceptibility to developing autoimmune disease. As used herein, "susceptibility to autoimmune disease" indicates a likelihood of at least greater than the average of developing autoimmune disease, and in some embodiments at least about 10% greater. Thus the invention also includes systems and methods for treating a subject having autoimmune disease to reduce associated cell death.

When used with mammalian cells in vitro, certain systems and methods may have utility for loading of specific antigens within the MHC molecules. Cells with specific antigen loading in class II molecules have utility in a variety of analytical and diagnostic assays. These cells are also useful as therapeutic agents. For instance, the cells can be used in culture to study immune responses or to screen the effect of putative drugs on inhibiting or promoting antigen-specific immune responses. Additionally, the cells could be administered to a mammalian subject to promote an antigen-specific T cell response. When administered to a subject, the class II MHC/antigen complexes on the surface of the cell can interact with endogenous T cells, inducing an immune cascade, and thus can produce an antigen-specific immune response. In some embodiments, the cells manipulated in vitro have been isolated from the same subject ex vivo.

The systems and methods of the invention can also be used for treating a mammalian subject in vivo to induce an antigen-specific immune response. It is useful to produce antigen-specific immune responses against any foreign antigen, whether it is capable of causing a pathological state and/or any damage to its mammalian host. The terms "foreign antigen" or "antigen" are used synonymously to refer to a molecule capable of provoking an immune response in a host, wherein the antigen is not a self-antigen, as defined above.

Thus, these terms specifically excludes self-antigens. Self-antigens are used herein to refer to the peptide-antigens of autoimmune disorders. An immune response against the self-antigen results in an autoimmune disorder. The term "self-antigen" does not include, however, antigens such as cancer antigens, which are recognized by the host as foreign and which are not associated with autoimmune disease. Thus, the term "antigen" specifically excludes self-antigens and broadly includes any type of molecule (e.g. associated with a host or foreign cell) that is recognized by a host immune system as being foreign. Antigens include, but are not limited to, cancer antigens and microbial antigens and may be composed of cells, cell extracts, polysaccharides, polysaccharide conjugates, lipids, glycolipids, carbohydrates, peptides, proteins, viruses, viral extracts, etc. A "cancer antigen," as used herein, is a compound which is associated with a tumor or cancer cell surface and which is capable of provoking an immune response when expressed on the surface of an antigen-presenting cell in the context of a class II MHC molecule. Cancers or tumors include those described above.

Cancer antigens include but are not limited to Melan-A/MART-1, Dipeptidyl peptidase W (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, alpha-fetoprotein, E-cadherin, alpha-catenin, beta-catenin and gamma-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1 and CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, or c-erbB-2.

In some embodiments, cancers or tumors escaping immune recognition and tumor-antigens associated with such tumors (but not exclusively), include acute lymphoblastic leukemia (etv6, aml1, cyclophilin b), B cell lymphoma (Ig-idiotype), glioma (E-cadherin, alpha-catenin, beta-catenin, gamma-catenin, p120ctn), bladder cancer (p21ras), billiary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-C017-1A/GA733, APC), choriocarcinoma (CEA), epithelial cell-cancer (cyclophilin b), gastric cancer (HER2/neu, c-erbB-2, ga733 glycoprotein), hepatocellular cancer (alpha-fetoprotein), hodgkins lymphoma (imp-1, EBNA-1), lung cancer (CEA, MAGE-3, NY-ESO-1), lymphoid cell-derived leukemia (cyclophilin b), melanoma (p15 protein, gp75, oncofetal antigen, GM2 and GD2 gangliosides), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its immunogenic epitopes PSA-1, PSA-2, and PSA-3, PSMA, HER2/neu, c-erbB-2), pancreatic cancer (p21ras, MUC family, HER2/neu, c-erbB-2, ga733 glycoprotein), renal (HER2/neu, c-erbB-2), squamous cell cancers of cervix and esophagus (viral products such as human papilloma virus proteins), testicular cancer (NY-ESO-1), T cell leukemia (HTLV-1 epitopes), and melanoma (Melan-A/MART-1, cdc27, MAGE-3, p21ras, gp100$^{Pmel117}$).

For examples of tumor antigens which bind to either or both MHC class I and MHC class II molecules, see the following references: Coulie, *Stem Cells*, 13:393-403, 1995, Traversari, et al., *J. Exp. Med.*, 176:1453-1457, 1992, Chaux, et al., *J. Immunol.*, 163:2928-2936, 1999, Fujie, et al., *Int. J. Cancer*, 80:169-172, 1999, Tanzarella, et al., *Cancer Res.*, 59:2668-2674, 1999, van der Bruggen, et al., *Eur. J. Immunol.*, 24:2134-2140, 1994, Chaux, et al., *J. Exp. Med.*, 189:767-778, 1999, Kawashima et al, *Hum. Immunol.*, 59:1-14, 1998, Tahara, et al., *Clin. Cancer Res.*, 5:2236-2241, 1999, Gaugler, et al., *J. Exp. Med.*, 179:921-930, 1994, van der Bruggen, et al., *Eur. J. Immunol.*, 24:3038-3043, 1994, Tanaka, et al., *Cancer Res.*, 57:4465-4468, 1997, Oiso, et al., *Int. J. Cancer*, 81:387-394, 1999, Herman, et al., *Immunogenetics*, 43:377-383, 1996, Manici, et al., *J. Exp. Med.*, 189:871-876, 1999, Duffour, et al., *Eur. J. Immunol.*, 29:3329-3337, 1999, Zorn, et al., *Eur. J. Immunol.*, 29:602-607, 1999, Huang, et al., *J. Immunol.*, 162:6849-6854, 1999, Boël, et al., *Immunity*, 2:167-175, 1995, Van den Eynde, et al., *J. Exp. Med.*, 182:689-698, 1995, De Backer, et al., *Cancer Res.*, 59:3157-3165, 1999, Jäger, et al., *J. Exp. Med.*, 187:265-270, 1998, Wang, et al., *J. Immunol.*, 161:3596-3606, 1998, Aarnoudse, et al., *Int. J. Cancer*, 82:442-448, 1999, Guilloux, et al., *J. Exp. Med.*, 183:1173-1183, 1996, Lupetti, et al., *J. Exp. Med.*, 188:1005-1016, 1998, Wölfel, et al., *Eur. J. Immunol.*, 24:759-764, 1994, Skipper, et al., *J. Exp. Med.*, 183:527-534, 1996, Kang, et al., *J. Immunol.*, 155:1343-1348, 1995, Morel, et al., *Int. J. Cancer*, 83:755-759, 1999, Brichard, et al., *Eur. J. Immunol.*, 26:224-230, 1996, Kittlesen, et al., *J. Immunol.*, 160:2099-2106, 1998, Kawakami, et al., *J. Immunol.*, 161:6985-6992, 1998, Topalian, et al., *J. Exp. Med.*, 183:1965-1971, 1996, Kobayashi, et al., *Cancer Res.*, 58:296-301, 1998, Kawakami, et al., *J. Immunol.*, 154:3961-3968, 1995, Tsai, et al., *J. Immunol.*, 158:1796-1802, 1997, Cox, et al., *Science*, 264:716-719, 1994, Kawakami, et al., *Proc. Natl. Acad. Sci. U.S.A.*, 91:6458-6462, 1994, Skipper, et al, *J. Immunol.*, 157:5027-5033, 1996, Robbins, et al., *J. Immunol.*, 159:303-308, 1997, Castelli et al, *J. Immunol.*, 162:1739-1748, 1999, Kawakami, et al., *J. Exp. Med.*, 180:347-352, 1994, Castelli, et al., *J. Exp. Med.*, 181:363-368, 1995, Schneider, et al., *Int. J. Cancer*, 75:451-458, 1998, Wang, et al., *J. Exp. Med.*, 183:1131-1140, 1996, Wang, et al., *J. Exp. Med.*, 184:2207-2216, 1996, Parkhurst, et al., *Cancer Res.*, 58:4895-4901, 1998, Tsang, et al., *J. Natl. Cancer Inst.*, 87:982-990, 1995, Correale, et al., *J. Natl. Cancer Inst.*, 89:293-300, 1997, Coulie, et al., *Proc. Natl. Acad. Sci. U.S.A.*, 92:7976-7980, 1995, Wölfel, et al., *Science*, 269:1281-1284, 1995, Robbins, et al., *J. Exp. Med.*, 183:1185-1192, 1996, Brändle, et al., *J. Exp. Med.*, 183:2501-2508, 1996, ten Bosch, et al., *Blood*, 88:3522-3527, 1996, Mandruzzato, et al., *J. Exp. Med.*, 186:785-793, 1997, Guéguen, et al., *J. Immunol.*, 160:6188-6194, 1998, Gjertsen, et al., *Int. J. Cancer*, 72:784-790, 1997, Gaudin, et al., *J. Immunol.*, 162:1730-1738, 1999, Chiari, et al., *Cancer Res.*, 59:5785-5792, 1999, Hogan, et al., *Cancer Res.*, 58:5144-5150, 1998, Pieper, et al., *J. Exp. Med.*, 189:757-765, 1999, Wang, et al., *Science*, 284:1351-1354, 1999, Fisk, et al., J. Exp. Med.

181:2109-2117, 1995, Brossart, et al., *Cancer Res.*, 58:732-736, 1998, Röpke, et al., *Proc. Natl. Acad. Sci. U.S.A.*, 93:14704-14707, 1996, Ikeda, et al., *Immunity* 6:199-208, 1997, Ronsin, et al., *J. Immunol.*, 163:483-490, 1999, or Vonderheide, et al., *Immunity*, 10:673-679, 1999. These antigens as well as others are disclosed in PCT Application PCT/US98/18601.

The systems and methods of the invention are also useful for treating mammals at risk of, or afflicted with, allergic responses. An "allergic response" as used herein is a disorder in which the host's immune response to a particular antigen is unnecessary or disproportionate, resulting in pathology. An allergic response may occur, in part, because a T cell recognizes a particular class II MHC/peptide complex and triggers a cascade of immune response. If the class II MHC/peptide complex is inhibited from being formed, the allergic response is reduced or suppressed. Any allergic response in which class II MHC/peptide complexes play a role may be treated according to the methods of the present invention. Allergies arising from an allergic response include, but are not limited to, allergies to pollen, ragweed, shellfish, domestic animals, (e.g., cats and dogs), B-venom, and the like. A subset of allergic responses produce asthma. Allergic asthmatic responses are also included within the definition of the term "allergic response." It is particularly desirable to treat severe or life-threatening allergic responses, such as those arising during asthmatic attacks or anaphylactic shock, according to the systems and methods of the invention.

In another aspect, the systems and methods of the invention are also useful for treating mammals that have undergone or are about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic immune response" against the donor tissues which results from the presence of non-self or allogeneic class II MHC molecules presenting antigenic peptides on the surface of donor cells.

The systems and methods of the invention, in yet another aspect, are useful for treating mammals having an inflammatory disease or condition. An "inflammatory disease or condition," as used herein, refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include, but are not limited to, meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

In one aspect, the compositions of the invention can also be used in combination with other therapies, such as radiation therapy. When a combination of therapies are used the effective amount to achieve the desired result, inhibition of cell proliferation may be less. This may reduce or eliminate any side effects associated with high concentrations of the individual therapies. One example is a combination of one or more compositions of the invention and radiation therapy. In some cases, the radiation therapy may also contribute to the inhibition of UCP in the plasma membrane. Radiation-sensitive cells are those cells that express UCP in the plasma membrane, and radioresistant cells do not express plasma membrane UCP. The invention also includes, in some instances, systems and methods of treating radioresistant cells by inducing UCP expression in the plasma membrane and treating them with radiation.

Optionally, in some embodiments, a targeting mechanism can be used to target one or more compositions of the invention to a specific cell, tumor, wound, or the like. It is desirable in many instances to specifically target a cell type to increase the efficiency and specificity of administration of the composition, thus avoiding the effects that can damage or destroy unrelated cells. Thus, a delivery system that enables the delivery of such drugs specifically to target cells is provided. The delivery system may increase the efficacy of treatment and reduce the associated "side effects" of such treatment.

Methods of targeting drugs and other compositions to target cells (such as cancer cells or cells within a wound) are well known in the art. One method of targeting involves antibody or receptor targeting. Receptor or antibody targeting involves linking the compound of the invention to a ligand or an antibody that has an affinity for a receptor or cell surface molecule expressed on the desired target cell surface, for example, UCP. Using this approach, a composition of the invention is intended to adhere to the target cell following formation of a ligand-receptor or antibody-cell surface antigen complex on the cell surface. The type of receptor or antibody used to target the cell will depend on the specific cell type being targeted. A target molecule may be attached by a peptide or other type of bond such as a sulfhydryl or disulfide bond. Targeting molecules are described, for instance in U.S. Pat. No. 5,849,718, as well as many other references.

In general, the targeting moiety can be coupled to a composition of the invention. The molecules may be directly coupled to one another, such as by conjugation, or may be indirectly coupled to one another where, for example, the targeting moiety is on the surface of a liposome and one or more compositions of the invention are contained within the liposome. If the molecules are covalently linked to one another, then the targeting moiety can be covalently or non-covalently bound to the compound of the invention in a manner that preserves the targeting specificity of the targeting moiety. As used herein, "linked" or "linkage" means two entities are bound to one another by any physiochemical means. It is important that the linkage be of such a nature that it does not impair substantially the effectiveness of the compositions of the invention or the binding specificity of the targeting moiety. Keeping these parameters in mind, While it is preferred that the linkage be a covalent link, any linkage known to those of ordinary skill in the art may be employed, covalent or noncovalent. Such means and methods of linkage are well known to those of ordinary skill in the art.

Linkages according to the invention need not be direct linkage. The compositions of the invention may be provided with functionalized groups to facilitate their linkage and/or linker groups may be interposed therebetween to facilitate their linkage. In some instances, the components of the present invention may be synthesized in a single process, whereby the composition is regarded as a single entity. For example, a targeting moiety specific for a tumor cell could be synthesized together with a VCP inhibitor and a fatty acid metabolism inhibitor of the invention. These and other modifications are intended to be embraced by the present invention.

Specific examples of covalent bonds include those where bifunctional cross-linker molecules can be used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available crosslinkers are reactive with one or more of the following groups, such as primary amines, secondary amines, sulfhydriles, carboxyls, carbonyls and carbohydrates.

Non-covalent methods of conjugation also may be used to join the targeting moiety and the composition in some cases. Non-covalent conjugation may be accomplished by direct or indirect means, including hydrophobic interaction, ionic interaction, intercalation, binding to major or minor grooves of a nucleic acid, and other affinity interactions.

Covalent linkages may be noncleavable in physiological environments, or cleavable in physiological environments, such as linkers containing disulfide bonds. Such molecules may resist degradation and/or may be subject to different intracellular transport mechanisms. One of ordinary skill in the art will be able to ascertain, without undue experimentation, the preferred bond for linking the targeting moiety and the compositions of the invention, based on the chemical properties of the molecules being linked and the preferred characteristics of the bond, for a given application.

For indirect linkage, the targeting moiety may be part of a particle, such as a liposome, which is targeted to a specific cell type. The liposome, in turn, may contain the compositions of the invention. The manufacture of liposomes containing compositions of the invention is fully described in the literature. Many for example, are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (i.e., 12 to 20 carbons), for example, naturally occurring fatty acids of between 14 and 18 carbons in length. These molecules can be attached to one or more compositions of the invention, for example, with the lipophilic anchor inserting into the membrane of a liposome and the compositions tethered on the surface of the liposome for targeting the liposome to the cell. In other cases, one or more compositions of the invention may be present in the interior of the liposome.

Each of the compositions of the invention (or portions thereof) may optionally be associated with a delivery system or vector, in one aspect. In its broadest sense, a "vector" is any vehicle capable of facilitating: (1) delivery of a composition to a target cell or (2) uptake of a composition by a target cell, if uptake is important. Optionally, a "targeting ligand" (in addition to, or the same as, the plasma membrane targeting molecule) can be attached to the vector to selectively deliver the vector to a cell that expresses on its surface the cognate receptor for the targeting ligand. In this manner, the vector (containing one or more compositions of the invention) can be selectively delivered to a cell in, e.g., a tumor, a wound, etc. In general, the vectors useful in the invention are divided into two classes: colloidal dispersion systems and biological vectors. Other example compositions that can be used to facilitate uptake by a target cell of compositions of the invention include calcium phosphate and other chemical mediators of intracellular transport, microinjection compositions, and electroporation.

In general, the vectors useful in the invention include, but are not limited to, plasmids, phagemids, viruses, other vehicles derived from viral or bacterial sources that have been manipulated by the insertion or incorporation of the UCP and/or Fas inhibitor nucleic acid sequences. Viral vectors include, but are not limited to, nucleic acid sequences from any of the following viruses: retrovirus, such as moloney murine leukemia virus, harvey murine sarcoma virus, murine mammary tumor virus, and rouse sarcoma virus, adenovirus, adeno-associated virus, SV40-type viruses, polyoma viruses, Epstein-Barr viruses, papilloma viruses, herpes virus, vaccinia virus, polio virus, and RNA virus such as a retrovirus. One can readily employ other vectors not named above but known to the art.

In some cases, the viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in the literature, e.g., Kriegler, *Gene Transfer and Expression, A Laboratory Manual*, W.H. Freeman, Co., 1990 and Murry, Ed. *Methods in Molecular Biology*, Vol. 7, Humana Press, Inc., 1991.

A virus useful for certain applications is an adeno-associated virus, which is a double-stranded DNA virus. The adeno-associated virus can be engineered to be replication-deficient and is capable of infecting a wide range of cell types and species in many cases. It further has certain advantages, such as heat and lipid solvent stability, high transduction frequencies in cells of diverse lineages, including hemopoietic cells, and lack of superinfection inhibition, thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extra chromosomal Fashion.

Other suitable vectors include plasmid vectors. Plasmid vectors have been extensively described in the art and are well known to those of skill in the art. See e.g., Sambrook, et al., *Molecular Cloning: A Laboratory Manual*, Second Edition, Cold Spring Harbor Laboratory Press, 1989. Plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and/or ligation reactions to remove and add specific fragments of DNA.

It has also been discovered that gene-carrying plasmids can be delivered to the cells in vivo using bacteria. Modified forms of bacteria such as Salmonella can be transfected with the plasmid and can thus be used as delivery vehicles in some cases. The bacterial delivery vehicles can be administered to a host subject orally or by other administration means. The bacteria in some instances can pass through the gut barrier.

High levels of expression have been established using this methodology.

Compaction agents also can be used alone, or in combination with, a vector of the invention. A "compaction agent," as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the compositions in a form that is more efficiently taken up by the cell or, more preferably, in combination with one or more of the above-described vectors.

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. The dose to the subject may be such that a therapeutically effective amount of one or more active compounds reaches the active site(s) within the subject. A "therapeutically effective" or an "effective" dose, as used herein, means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health, the composition used, the type of delivery system used, the time of administration relative to the severity of the disease, and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to eliminate or at least control a cancer or a wound, and/or to reduce the severity of the cancer or wound. The pharmaceutical preparations of the invention are administered to subjects in effective amounts. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day.

As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound, when parentally administered, may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day.

In some embodiments, the concentration of the active compound(s) of the composition, if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. If applied topically, the concentration may be about 0.1 mg to about 500 mg/g of ointment or other base, about 1.0 mg to about 100 mg/g of base, or about 30 mg to about 70 mg/g of base. The specific concentration partially depends upon the particular composition used, as some are more effective than others. The dosage concentration of the composition actually administered is dependent, at least in part, upon the particular disorder being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously effect the mammal.

The dosage may be given in some cases at the maximum amount while avoiding or minimizing any potentially detrimental side effects within the subject. The dosage actually administered can be dependent upon factors such as the final concentration desired at the active site, the method of administration to the subject, the efficacy of the composition, the longevity of the composition within the subject, the mode and/or timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, active site of the cancer or wound, or current state of health of the subject may also influence the dose required and/or the concentration of the composition at the active site. Variations in dosing may occur between different individuals or even within the same individual on different days. These factors are well known to those of ordinary skill in the art and can be addressed with no more than routine experimentation. It is preferred that a maximum dose be used, that is, the highest safe dose according to sound medical judgment.

In the event that the response of a particular subject is insufficient at such doses, even higher doses (or effectively higher doses by a different, more localized delivery route) may be employed to the extent that subject tolerance permits. Multiple doses per day are also contemplated, in some cases, to achieve appropriate systemic levels within the subject or within the active site of the subject. In certain instances, dosing amounts, dosing schedules, routes of administration, and the like may be selected as described herein, whereby therapeutically effective levels of the composition are provided.

In certain embodiments where cancers are being treated, a composition of the invention is administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method that allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the composition. Other oral compositions suitable for use with the invention include solutions or suspensions in aqueous or non-aqueous liquids such as a syrup, an elixir, or an emulsion. In one set of embodiments, the composition may be used to fortify a food or a beverage.

Injections can be e.g., intravenous, intradermal, subcutaneous, intramuscular, or interperitoneal. For example, the inhibitor can be injected intravenously or intramuscularly for the treatment of multiple sclerosis, or can be injected directly into the joints for treatment of arthritic disease, or can be injected directly into the lesions for treatment of pemphigus vulgaris. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. For systemic administration, it may be useful to encapsulate the composition in liposomes.

Inhalation includes administering the composition with an aerosol in an inhaler, either alone or attached to a carrier that can be absorbed.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), polyvinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those of ordinary skill in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth) acrylic acid, polyamides, copolymers and mixtures thereof.

Bioadhesive polymers of particular interest in some cases include, but are not limited to, the bioerodible hydrogels described by Sawhney, et al., *Macromolecules,* 26:581-587, 1993, the teachings of which are incorporated herein, as well as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The systems and methods of the invention can be administered by any method that allows the composition of the invention to reach the target cells, e.g., tumor cells. These methods include, e.g., injection, infusion, deposition, implantation, anal or vaginal supposition, oral ingestion, inhalation, topical administration, or any other method of administration where access to the target cells by the inhibitor is obtained. In some embodiments, topical administration is preferred, due to the high concentration of APCs in the skin. One method for accomplishing topical administration includes transdermal administration, such as iontophoresis. Iontophoretic transmission can be accomplished by using commercially-available patches that deliver a compound continuously through unbroken skin for periods of hours to days to weeks, depending on the particular patch. This method allows for the controlled delivery of the composition through the skin in relatively high concentrations. One example of an iontophoretic patch is the LECTRO PATCH™ sold by General Medical Company of Los Angeles, Calif. The patch provides dosages of different concentrations that can be continuously or periodically administered across the skin using electronic stimulation of reservoirs containing the composition. Topical administration also includes epidermal administration, which involves the mechanical or chemical irritation of the outermost layer of the epidermis sufficiently to provoke an immune response to the irritant. The irritant attracts APCs to the site of irritation where they can then take up the composition. One example of a mechanical irritant is a tyne-containing device. Such a device contains tynes that irritate the skin and deliver the drug at the same time, for instance, the MONO VACC™ manufactured by Pasteur Merieux of Lyon, France. The device contains a syringe plunger at one end and a tyne disk at the other. The tyne disk supports several narrow diameter tynes, which are capable of scratching the outermost layer of epidermal cells. Chemical irritants include, for instance, keratinolytic agents, such as salicylic acid, and can be used alone or in conjunction with other irritants such as mechanical irritants.

In certain embodiments of the invention, the administration of the composition of the invention may be designed so as to result in sequential exposures to the composition over a certain time period, for example, hours, days, weeks, months, or years. This may be accomplished, for example, by repeated administration of a composition of the invention by one of the methods described above, and/or by a sustained or controlled release delivery system in which the composition is delivered over a prolonged period, usually without repeated administrations. Administration of the composition using such a delivery system may be, for example, by oral dosage forms, bolus injections, transdermal patches or subcutaneous implants. Maintaining a substantially constant concentration of the composition may be desirable in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides, hydrogel release systems, liposome-based systems, phospholipid based-systems, silastic systems, peptide based systems, wax coatings, compressed tablets using conventional binders and excipients, or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and 5,239,660), or diffusional systems in which an active component controls the release rate (for example, as described in U.S. Pat. Nos. 3,832,253, 3,854,480, 5,133,974 and 5,407,686). The formulation may be present as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention in some cases.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core-degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In certain embodiments of the invention, a composition may include a suitable pharmaceutically acceptable carrier, for example, as incorporated into a liposome, incorporated into a polymer release system, or suspended in a liquid, e.g., in a dissolved form or a colloidal form, such as in a colloidal dispersion system. In general, pharmaceutically acceptable carriers suitable for use in the invention are well known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The term "carrier" denotes an organic or inorganic ingredient, which may be natural or synthetic, with which one or more active compounds of the invention are combined to facilitate the application of the composition. The carrier may be co-mingled or otherwise mixed with one or more active compounds of the present invention, and with each other, in a manner such that there is no interaction that would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

As used herein, a "colloidal dispersion system" refers to a natural or synthetic molecule, other than those derived from bacteriological or viral sources, capable of delivering to and releasing the composition in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels that are useful as a delivery vector in vivo or in vitro. It has been shown that large unilamellar vessels (LUV), which range in size from 0.2 micrometers to 4.0 micrometers can encapsulate large macromolecules within the aqueous interior and these macromolecules can be delivered to cells in a biologically active form (Fraley, et al., *Trends Biochem. Sci.*, 6:77, 1981).

Lipid formulations for transfection are commercially available, e.g., from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2,3-dioleyloxy)-propyl],N,N-trimethylammonium chloride (DOTMA) and dimethyl dioctadecylammonium bromide (DDAB). Methods for making liposomes are well known in the art and have been described in many publications. Some liposomes were described in a review article by Gregoriadis, *Trends in Biotechnol.*, 3:235-241, 1985, which is hereby incorporated by reference.

In one embodiment, the vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System." PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the present invention, the compositions of the invention described herein can be encapsulated or dispersed within the biocompatible, optionally biodegradable polymeric matrix disclosed in PCT/US/03307.

The polymeric matrix can be in the form of a microparticle such as a microsphere (where the composition is dispersed throughout a solid polymeric matrix) or a microcapsule (where the composition is stored in the core of a polymeric shell). Other forms of the polymeric matrix for containing the composition include films, coatings, gels, implants, and stents. The size and composition of the polymeric matrix device can be selected to result in favorable release kinetics in the tissue into which the matrix is introduced. The size of the polymeric matrix can also be selected according to the method of delivery which is to be used, typically injection into a tissue or administration of a suspension by aerosol into the nasal and/or pulmonary areas. When an aerosol route is used the polymeric matrix and composition can be encompassed in a surfactant vehicle. The polymeric matrix composition can be selected to have both favorable degradation rates and/or to be formed of a material that is bioadhesive, e.g., to further increase the effectiveness of transfer when the matrix is administered to a nasal and/or pulmonary surface that has sustained an injury. The matrix composition can also be selected not to degrade, but rather, to release by diffusion over an extended period of time. In another embodiment, the matrix is a biocompatible microsphere that is suitable for oral delivery. Such microspheres are disclosed in Chickering, et al., *Biotech. and Bioeng.*, 52:96-101, 1996, and Mathiowitz, et al., *Nature*, 386:410-414, 1997.

Both non-biodegradable and biodegradable polymeric matrices can be used to deliver the compositions of the invention to the subject. Such polymers may be natural or synthetic polymers. The polymer may be selected based on the period of time over which release is desired, generally in the order of a few hours, to a year or longer. Typically, release over a period ranging from between a few hours and three to twelve months is desirable. The polymer optionally is in the form of a hydrogel that can absorb up to about 90% of its weight in water and further, optionally is cross-linked with multivalent ions or other polymers.

In some embodiments, the compositions of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate, granulating and disintegrating agents such as corn starch or algenic acid, binding agents such as starch, gelatin or acacia, lubricating agents such as magnesium stearate, stearic acid, or talc, time-delay materials such as glycerol monostearate or glycerol distearate, suspending agents such as sodium carboxymethylcellulose, methylcellulose, hydroxypropylmethylcellulose, sodium alginate, polyvinylpyrrolidone, dispersing or wetting agents such as lecithin or other naturally-occurring phosphatides, thickening agents such as cetyl alcohol or beeswax, buffering agents such as acetic acid and salts thereof, citric acid and salts thereof, boric acid and salts thereof, or phosphoric acid and salts thereof, or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in, for example, *Remington's Pharmaceutical Sciences*, Mack Publishing Co. Those of ordinary skill in the art can readily determine the various parameters for preparing and formulating the compositions of the invention without resort to undue experimentation.

In some embodiments, the present invention includes the step of forming a composition of the invention by bringing an active compound into association or contact with a suitable carrier, which may constitute one or more accessory ingredients. The final composition may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts, or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

In one aspect, the present invention provides any of the above-mentioned compositions in kits, optionally including instructions for use of the composition e.g., for the treatment of cancers or wounds. That is, the kit can include a description of use of the composition for participation in any biological or chemical mechanism disclosed herein associated with cancers or wounds. The kits can further include a description of activity of the cancers or wounds in treating the pathology, as opposed to the symptoms. The kit can include a description of use of the compositions as discussed herein. The kit also can include instructions for use of a combination of two or more compositions of the invention, or instruction for use of a combination of a composition of the invention and one or more other compounds indicated for treatment of a cancer, a wound, etc. Instructions also may be provided for administering the composition by any suitable technique as previously described, for example, orally, intravenously, pump or implantable delivery device, or via another known route of drug delivery.

The invention also involves, in another aspect, promotion of the treatment of cancers, wounds, etc. according to any of the systems or methods described herein. In some embodiments, one or more compositions of the invention may be promoted for treatment of cancers or wounds, or include instructions for treatment of cancers or wounds. In some cases, the invention provides a method involving promoting the prevention or treatment of cancers, wounds, etc. via administration of any one of the compositions of the present invention, and homologs, analogs, derivatives, enantiomers and functionally equivalent compositions thereof in which the invention is able to treat cancer, wounds, etc. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancers or wounds. "Instructions" can define a component of promotion, and typically involve written instructions on or associated with packaging of compositions of the invention. Instructions also can include any oral or electronic instructions provided in any manner. The "kit" typically defines a package including one or more compositions of the invention and the instructions, or homologs, analogs, derivatives, enantiomers and functionally equivalent compositions thereof, but can also include a composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting or administering the components to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition and the mode of use or administration. Suitable solvents are well known, for example as previously described, and are available in the literature. The solvent will depend on the compound and the mode of use or administration.

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure.

The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A composition, comprising:
a pharmacon comprising a combination of, or a bifunctional compound that links, a glycolysis inhibitor that is, or that is derived from, hypoglycin A, and a fatty acid metabolism inhibitor, wherein the fatty acid metabolism inhibitor is an oxirane carboxylic acid compound having the structure:

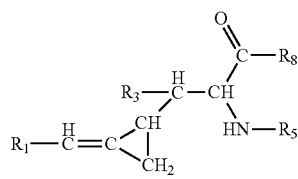

where $R_6$ and $R_7$ each represent a hydrogen atom, a halogen atom, a 1-4 carbon atom alkyl group, a 1-4 carbon atom alkoxy group, a nitro group or a trifluoromethyl group, $R_8$ represents a hydrogen atom or a 1-4 carbon atom alkyl group, Y represents $(CH_2)_k$ where k is from 2 to 8, 7 or the grouping $—O—(CH—)_m—$, m is 0 or a whole number from 1 to 4, n is a whole number from 2 to 8 wherein the sum of m and n is a whole number from 2 to 8.

2. The composition of claim 1 in which said glycolysis inhibitor has the structure:

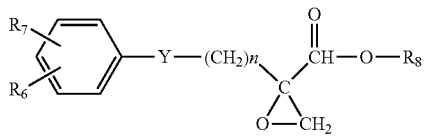

where $R_1$, $R_3$, and $R_5$ each represent a hydrogen atom, a 1-4 carbon atom alkyl group, a 1-4 carbon atom alkoxy group, a nitro group, or a trifluoromethyl group, and $R_8$ is as given above.

3. The composition of claim 2 in which the glycolysis inhibitor is hypoglycin A.

4. The composition of claim 1 in which the oxirane carboxylic acid compound is etomoxir.

5. The composition of claim 1 in which said pharmacon comprises a bifunctional compound that links a glycolysis inhibitor that is, or that is derived from, hypoglycin A, and a fatty acid metabolism inhibitor.

6. The composition of claim 5 in which the bifunctional compound links a moiety having the functionality of an oxirane carboxylic acid compound to a moiety having the functionality of hypoglycin or a hypoglycin A derivative.

* * * * *